(12) United States Patent
Eavri et al.

(10) Patent No.: US 11,788,146 B2
(45) Date of Patent: Oct. 17, 2023

(54) METHODS FOR THERAPEUTICS PRESCREENING IN BODILY FLUIDS

(71) Applicant: BARCODE DIAGNOSTICS LTD., Nazareth (IL)

(72) Inventors: Ronen Eavri, Binyamina (IL); Annie Sabbah, Haifa (IL); Felix Badinter, Karmiel (IL); Raphael Tshuva, Nesher (IL); Avi Schroeder, Binyamina (IL)

(73) Assignee: BARCODE DIAGNOSTICS LTD., Nazareth (IL)

( * ) Notice: Subject to any disclaimer, the term of this patent is extended or adjusted under 35 U.S.C. 154(b) by 439 days.

(21) Appl. No.: 16/628,210

(22) PCT Filed: Jul. 5, 2018

(86) PCT No.: PCT/IL2018/050736
§ 371 (c)(1),
(2) Date: Jan. 2, 2020

(87) PCT Pub. No.: WO2019/008590
PCT Pub. Date: Jan. 10, 2019

(65) Prior Publication Data
US 2020/0216907 A1    Jul. 9, 2020

Related U.S. Application Data

(60) Provisional application No. 62/529,023, filed on Jul. 6, 2017.

(51) Int. Cl.
*C12Q 1/6886* (2018.01)
*A61K 49/00* (2006.01)

(52) U.S. Cl.
CPC ............ *C12Q 1/6886* (2013.01); *A61K 49/00* (2013.01); *A61K 49/0017* (2013.01); *C12Q 2600/106* (2013.01); *C12Q 2600/136* (2013.01); *G01N 2800/52* (2013.01)

(58) Field of Classification Search
CPC ...... A61K 49/00; A61K 49/0017; C12Q 1/68; C12Q 1/6886; C12Q 2600/106; C12Q 2600/136; G01N 2800/52
USPC .......... 424/1.11, 1.49, 1.65, 1.69, 1.81, 1.85, 424/1.89, 9.1, 9.2, 9.6
See application file for complete search history.

(56) References Cited

U.S. PATENT DOCUMENTS

| 5,885,613 A | 3/1999 | Holland |
| 10,709,761 B2 * | 7/2020 | Schiffman ............... A61K 45/06 |
| 10,815,530 B2 * | 10/2020 | Schroeder ............ C12Q 1/6886 |

FOREIGN PATENT DOCUMENTS

| WO | 2016024281 A1 | 2/2016 |
| WO | 2016198609 A1 | 12/2016 |

OTHER PUBLICATIONS

Yaari et al (Nature Communications, published Nov. 10, 2016, pp. 1-10) (Year: 2016).*
Zvi Yaari et al. "Theranostic barcoded nanoparticles for personalized cancer medicine." Nature communications 7, 13325, Nov. 10, 2016.
Alexander L. Klibanov et al., "Amphipathic polyethyleneglycols effectively prolong the circulation time of liposomes", FEBS Letters, vol. 268 Issue 1 pp. 235-237, 1990.
Avi Schroeder et al.: "Remotely Activated Protein-Producing Nanoparticles", Nano Lett., vol. 12 Issue 6 pp. 2685-2689, 2012.
PCT Search Report for International Application No. PCT/IL2018/050736; dated Oct. 11, 2018 ; 3 pp.
PCT Written Opinion for International Application No. PCT/IL2018/050736; dated Oct. 11, 2018 ; 6 pp.
PCT Preliminary Report for International Application No. PCT/IL2018/050736; dated Jan. 7, 2020; 7 pp.
Nao Tokichi, Akira Ono. Protection and modification of synthetic nucleic acids for prodrug development. Drug Delivery System. Nov. 25, 2015;30(5):465-72.
Crowley, E. et al., "Liquid biopsy: monitoring cancer-genetics in the blood", Nature Reviews in Clinical Oncology, 10(8), pp. 472-484, Jul. 9, 2013 (Sep. 7, 2013). DOI: 10.1038/nrclinonc.2013.110.

* cited by examiner

*Primary Examiner* — D. L. Jones
(74) *Attorney, Agent, or Firm* — The Roy Gross Law Firm, LLC; Roy Gross

(57) ABSTRACT

A method for using bodily fluids in determining the cell-specific potency of drugs is provided. A composition comprising a plurality of types of carriers, wherein each carrier comprises a single-cell lethal amount of a therapeutic agent and a unique barcode identifying that agent and wherein the composition comprises equal numbers of each carrier type, equal concentrations of the agent and equal concentrations of each barcode is also provided. Further, methods useful for studying the therapeutic profile of one or more drugs within a cell microenvironment, including but not limited to a tumor, are provided.

16 Claims, 6 Drawing Sheets

METHODS FOR THERAPEUTICS PRESCREENING IN BODILY FLUIDS

CROSS-REFERENCE TO RELATED APPLICATIONS

This application is a National Phase of PCT Patent Application No. PCT/IL2018/050736 having International filing date of Jul. 5, 2018, which claims the benefit of priority of U.S. Provisional Patent Application No. 62/529,023, filed Jul. 6, 2017, and entitled "METHODS FOR THERAPEUTICS PRESCREENING IN BODILY FLUIDS" The contents of the above applications are all incorporated by reference as if fully set forth herein in their entirety.

FIELD OF INVENTION

The present invention is directed to assays useful in predicting personalized therapeutic potency and activity of therapeutic agents.

BACKGROUND OF THE INVENTION

Patients respond differently to medication; the success of a treatment depends greatly on selecting the right drug for each patient. 'Personalized Medicines' are aimed at addressing each patient's unique disease presentation. Diseases and disorders which require personalized medicine include malignant diseases, inflammatory diseases and neurodegenerative disease.

Cancer, as a non-limiting example, has a low actual response rate to medicines in the clinic. For example, less than 60% of breast, esophagus, colon or stomach-cancer patients respond to therapy; statistics decrease to less than 30% in patients with lung, melanoma, pancreatic, liver or recurrent ovarian cancers. Thus, selecting for the proper therapeutic, that will address each patient's unique disease presentation, can significantly improve the treatment outcome.

Genetic information and patient-specific biomarkers have helped advance personalized medicine. However, nearly 50% of patients still are mismatched with non-effective treatments, to then be categorized 'non-responders'.

Current methods of personalized treatment all require extraction of tissue from the patient. Such extractions, frequently in the form of a biopsy, are invasive to the patient, expensive to the care giver and sometimes impossible depending on the location of the disease. Further, cellular extraction runs the risk of only sampling some of the cells of the disease while missing others. This can be due to tumor metastasis, heterogeneity of a tumor, or the diffuse nature of a disease. Alternative methods of screening drugs for their patient-specific efficacy, that do not involve cellular extraction are greatly in need.

SUMMARY OF THE INVENTION

The present invention provides methods useful for predicting and determining the response of a subject afflicted with a disease to a therapeutic agent or combinations of therapeutic agents without the need for biopsy or tissue extraction.

The present invention presents for the first time a personalized approach enabling simultaneous screening of multiple therapeutic agents, for their patient specific potency, with only the extraction of bodily fluids and without biopsy. Thereby, the methods disclosed herein, grant physicians a new way of selecting drugs tailored for a single patient without the discomfort and cost of biopsy.

According to a first aspect, there is provided a method for predicting the response of a subject afflicted with a disease to at least one therapeutic agent, the method comprising the steps of:
(a) administering to the subject a composition comprising a plurality of types of carriers, each type of carrier independently comprises at least a single-cell lethal amount of at least one therapeutic agent and one or more barcodes uniquely identifying the at least one therapeutic agent;
(b) obtaining a fluid sample from the subject; and
(c) identifying, in the fluid, the efficacy of the at least one therapeutic agent by the presence of the unique barcode;
thereby predicting the response of a subject afflicted with a disease to a therapeutic agent.

According to some embodiments, the composition comprises a substantially equal number of each type of carrier. According to some embodiments, each type of carrier comprises a substantially equal barcode concentration. According to some embodiments, each type of carrier comprises a substantially equal concentration of the at least one therapeutic agent relative to an effective therapeutic dose (ETD) of the at least one therapeutic agent.

According to some embodiments, the at least one therapeutic agent is cytotoxic to a cell of the disease. According to some embodiments, the disease is cancer, and the at least one therapeutic agent is cytotoxic to cancer cells.

According to some embodiments, each type of carrier comprises a different at least one therapeutic agent.

According to some embodiments, the administration is intravenous injection and the composition comprises 1-200 of each type of carrier per a single disease cell of the subject. According to some embodiments, the administration is intratumoral injection, and the composition comprises 1-20 of each type of carrier per a single disease cell of the subject.

According to some embodiments, the obtaining is performed within a time frame of 48-192 hours following administration of the composition.

According to some embodiments, the barcode is a nucleic acid molecule and the identifying comprises sequencing the nucleic acid molecule. According to some embodiments, the barcode is a nucleic acid molecule and wherein the identifying comprises amplifying the nucleic acid molecule.

According to some embodiments, the fluid is selected from the group consisting of: blood, plasma, serum, saliva, urine, lymph, tumor fluid, breast milk, cerebral spinal fluid and seminal fluid. According to some embodiments, the fluid is blood.

According to some embodiments, the methods of the invention further comprise before step (a) obtaining a fluid sample from the subject and identifying the percentage of tumor DNA in the sample, and wherein the identifying the efficacy of the at least one therapeutic agent by the unique barcode comprises a comparison to the pre-administration tumor DNA percentage.

According to some embodiments, the methods of the invention further comprise removing intact cells from the fluid sample before step (c). According to some embodiments, the methods of the invention further comprise removing intact carrier from the fluid sample before step (c).

According to some embodiments, the at least one carrier further comprises a tag.

According to some embodiments, the unique barcode comprises a cleavage site specific to a nuclease specific to a cell of the disease. According to some embodiments, the unique barcode comprises a cleavage site specific to a nuclease with increased cytoplasmic localization in a cell of the disease.

According to some embodiments, the single-cell lethal amount is between 0.1% and 3% of the ETD.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
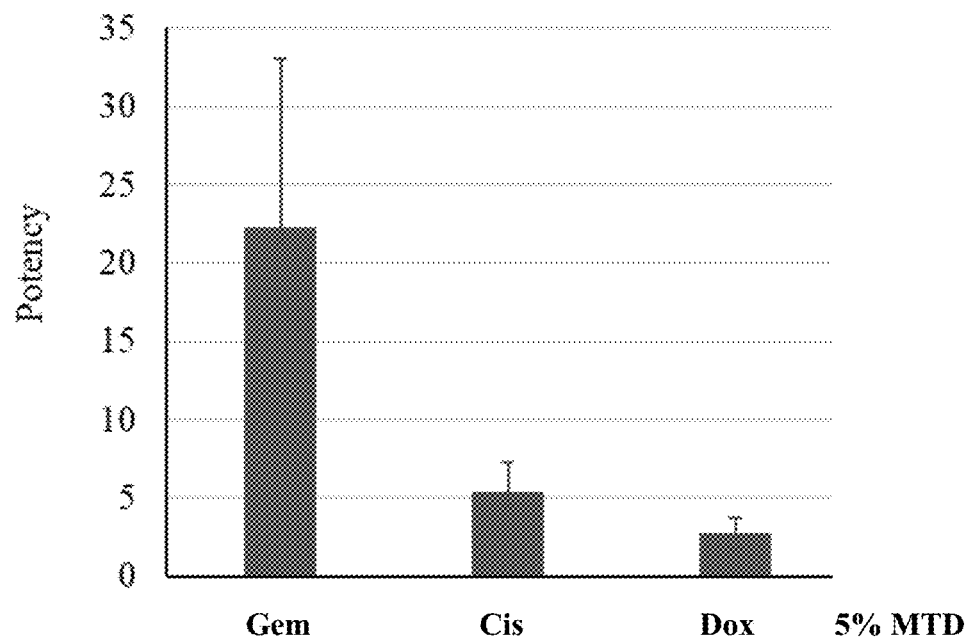
FIGS. 1A-C: Detection of barcodes from liposome mixes with equal relative drug concentrations. Bar charts showing the potency of gemcitabine, cisplatin and doxorubicin against triple negative breast cancer tumors when the drugs are provided at (1A) 5%, (1B) 1%, and (1C) 0.1% of the effective therapeutic dose (ETD). Potency of the drugs was defined as the ratio of the amount of a barcode in dead cells to the amount of that barcode in live cells.

The present invention provides methods useful for predicting and determining the therapeutic potency of a therapeutic agent or combinations of therapeutic agents against disease that do not require tumor biopsy, but rather can be performed from a liquid biopsy. The methods disclosed herein enable tailoring treatments to address each patient's unique disease presentation, without the requirement of extracting tissue from the patient.

The present invention also provides compositions useful for theranostic analysis, wherein the carrier number, drug concentration relative to the effective therapeutic dose (ETD) and barcode concentration are all substantially equal. Such compositions are advantageous in performing methods for predicting and determining therapeutic potency of combinations of therapeutic agents such as, but not limited to, the methods described herein.

As demonstrated herein below, carriers (e.g., nanoparticles) act as theranostic gauges for examining the therapeutic potency of a drug or drug combination inside a patient, prior to beginning a treatment cycle.

According to a first aspect, there is provided a composition comprising a plurality of types of carriers, each type of carrier independently comprising at least a single-cell lethal amount of at least one therapeutic agent and at least one barcode uniquely identifying the at least one therapeutic agent, wherein the composition comprises a substantially equal number of each type of carrier.

In some embodiments, the composition administered is a composition described in international patent publication WO2016024281 and wherein the composition comprises a substantially equal number of each type of carrier. In some embodiments, the compositions of the invention are for use in theranostic/diagnostic methods described in WO2016024281. In some embodiments, the compositions of the invention are for use in the theranostic/diagnostic methods described herein. In some embodiments, the compositions of the invention are for use in predicting the response of a subject afflicted with a disease to at least one therapeutic agent. In some embodiments, the compositions of the invention are for use in predicting the response of a subject afflicted with a disease to a plurality of therapeutic agents.

In some embodiments, the carriers comprise a therapeutic agent and a corresponding barcode, and optionally a tag. In some embodiments, each carrier contains an extremely low dose of a drug. In some embodiments, each carrier contains an extremely low dose of a drug, sufficient to treat only one cell, and far below the whole-body therapeutic threshold. In some embodiments, each carrier comprises a substantially equal concentration of the at least one therapeutic agent. In some embodiments, each carrier comprises a substantially equal concentration of the at least one therapeutic agent relative to a effective therapeutic dose (ETD) of the at least one therapeutic agent. In some embodiments, each carrier comprises less than 10%, 7%, 5%, 3%, 2%, 1%, 0.5%, or 0.1% of the MTD for the at least one therapeutic agent. Each possibility represents a separate embodiment of the invention. In some embodiments, each carrier comprises between 0.1-10%, 0.1-7%, 0.1-5%, 0.1-3%, 0.1-2%, 0.1-1%, 0.5-10%, 0.5-7%, 0.5-5%, 0.5-3%, 0.5-2%, 0.5-1%, 1-10%, 1-7%, 1-5%, 1-3%, or 1-2% of the MTD for the at least one therapeutic agent. Each possibility represents a separate embodiment of the invention.

As used herein, "ETD" refers to the medically approved dose of a drug or combination of drugs that produces a desired effect. Such doses for various drugs are well known to those skilled in the art and are available from numerous sources such as www.drugs.com and reference.medscape.com to name but a few. In some embodiments, the ETD is the minimum effective therapeutic dose (METD). The METD is the lowest possible dose that produces the desired effect. A skilled artisan will appreciate that such effective doses are for treating a subject as a whole. For the diagnostic/theranostic purposes of the invention treatment of an entire condition is not required, but rather just treatment of a few cells.

In some embodiments, the composition comprises at least one carrier, the at least one carrier comprises: a therapeutically effective amount of at least one therapeutic agent; a nucleic acid molecule uniquely identifying the at least one therapeutic agent; and optionally a tag (i.e., a tracer).

In some embodiments, the at least one therapeutic agent and the nucleic acid molecule, are encapsulated within the at least one carrier. In some embodiments wherein the carrier further comprises a tag, the at least one therapeutic agent, the nucleic acid molecule, and the tag are encapsulated within the at least one carrier. In some embodiments wherein the carrier further comprises a tag, the at least one therapeutic agent, and the nucleic acid molecule, are encapsulated within the at least one carrier and the tag is anchored onto the carrier. In some embodiments wherein the carrier further comprises a tag, the at least one therapeutic agent, and the nucleic acid molecule, are encapsulated within the at least one carrier and the tag is encapsulated within the at least one carrier or anchored onto the at least one carrier. In some embodiments, the tag is anchored onto the carrier's membrane.

In another embodiment, the composition comprises a plurality of carriers, each carrier independently comprises at least one therapeutic agent and a nucleic acid molecule uniquely identifying said at least one therapeutic agent. In some embodiments, the composition comprises 1-5 types of carriers independently comprising a therapeutic agent or combination thereof. In some embodiments, the composition comprises 1-10 types of carriers independently comprising a therapeutic agent or combination thereof. In some embodiments, the composition comprises 1-100 types of carriers independently comprising a therapeutic agent or combination thereof. In some embodiments, the composition comprises 1-200 carriers independently comprising a therapeutic agent or combination thereof. In some embodiments, the composition comprises 1-300, 1-400, 1-500, 1-600, 1-700, 1-750, 1-800, 1-900, 1-1000, 1-1200, 1-1400, 1-1500, 1-1600, 1-1750, 1-1800, or 1-2000 carriers independently comprising a therapeutic agent or combination thereof. Each possibility represents a separate embodiment of the invention. In some embodiments, the composition comprises 2-500 types of carriers independently comprising a therapeutic agent or combination thereof. As such, the methods of the invention provide simultaneous screening of multiple therapeutic agents or combinations thereof at a single cell resolution. In some embodiments, the methods of the invention provide simultaneous screening of onco-therapeutic agents or combinations thereof at a single cell resolution.

As used herein "types of carriers" refers to carriers comprising different therapeutic agents, or combinations of therapeutic agents. In some embodiments, the composition comprises at least two types of carriers. In some embodiments, the composition comprises at least 3 types of carriers.

In some embodiments, the types of carriers are all the same carrier, with different therapeutic agents or combinations of therapeutic agents. In some embodiments, the carrier is a liposome. In some embodiments, each type of carrier is the same type of liposome. In some embodiments, each type of liposome comprises the same lipid make up. In some embodiments, each type of liposome comprises an equal or substantially equal size, volume or diameter. Each possibility represents a separate embodiment of the invention. In some embodiments, each type of liposome comprises the same lipid concentration. In some embodiments, each type of liposome comprises a substantially equal lipid concentration. In some embodiments, each type of carrier comprises a substantially equal barcode concentration. In some embodiments, each type of carrier comprises an equal barcode concentration. In some embodiments, each type of carrier comprises a substantially equal concentration of the at least one therapeutic agent. In some embodiments, each type of carrier comprises a substantially equal concentration of the at least one therapeutic agent relative to MED or MTD of the at least one therapeutic agent. In some embodiments, each type of carrier comprises a substantially equal relative dose of the at least one therapeutic agent. In some embodiments, each type of carrier comprises an equal concentration of the at least one therapeutic agent relative to MED or MTD of the at least one therapeutic agent. In some embodiments, each type of carrier comprises an equal relative dose of the at least one therapeutic agent.

In some embodiments, substantially equal is equal. In some embodiments, substantially equal is equal within the ability to measure a parameter. In some embodiments, substantially equal is equal with the ability to produce the carriers. In some embodiments, substantially equal is at most a variance of 1, 2, 3, 5, 7, 10, 15, 20, 25 or 30%. Each possibility represents a separate embodiment of the invention. In some embodiments, substantially equal is at most a variance of 10%. In some embodiments, the number of each type of carriers is equal or as close to equal as possible. In some embodiments, the number of carriers is equal, and the concentrations of barcodes and relative therapeutic agent concentrations are made as close to equal as possible while keeping the number of carriers equal. In some embodiments, the number of carriers in each type is equal and the barcode concentration and/or therapeutic agent relative concentration are substantially equal.

As detailed hereinbelow, the number of carriers in each type of carrier should be equal so as to not introduce a bias towards one type of carrier (and thereby to one therapeutic agent). When the carriers are liposomes with equal size and the same lipid content (same percentage of each lipid component) the total lipid concentration is proportional to the carrier number. Thus, measuring the lipid concentration of each type of liposome also mixing of different types of carriers such that they will have the same total number of carriers. The amount of drug loaded into each type of carrier can be modified so that when equal numbers of carriers are mixed, the relative dose (based on MED) of each therapeutic ends up roughly equal. In some embodiments, the substantially equal lipid concentration comprises a variance of at most 0.1%, 0.5%, 1%, 2%, 3%, 4%, 5%, 6%, 7%, 8%, 9%, 10%, 12%, 15%, 17%, or 20%. Each possibility represents a separate embodiment of the invention. In some embodiments, the substantially equal lipid concentration comprises a variance of at most 1%. In some embodiments, the lipid concentration of the liposomes is between 20-55, 20-50, 20-45, 20-40, 25-55, 25-50, 25-45, 25-40, 30-55, 30-50, 30-45, or 30-40 mM. Each possibility represents a separate embodiment of the invention. In some embodiments, the lipid concentration of the liposomes is between 30-45 mM. In some embodiments, the lipid concentration of the liposomes is between 30-55 mM.

In some embodiments, the composition comprises at least two types of carriers. In some embodiments, the composition comprises at least 3 types of carriers.

Therapeutic Agents

In some embodiments, the therapeutic agent treats a disease or condition with which a subject is afflicted. In some embodiments, the therapeutic agent targets specific cells. In some embodiments, the therapeutic agent is cytotoxic to its target cells. In some embodiments, the therapeutic agent kills its target cells. In some embodiments, the therapeutic agent induces cell death in its target cells. In some embodiments, the therapeutic agent induces apoptosis in its target cells. In some embodiments, the therapeutic agent induces necrosis in its target cells. In some embodiments, the therapeutic agent induces apoptosis or necrosis in its target cells. In some embodiments, the therapeutic agent treats cancer. In some embodiments, the therapeutic agent kills cancer cells. In some embodiments, therapeutic agent is suspected of killing cancer cells. The skilled artisan will appreciate that the compositions and methods of the invention are for use in testing for personalized treatment. As such the therapeutic agent may be any drug or combination of drugs that might be able to treat a patient. Even theoretical or hypothetical treatment agents may be used as use of the assay of the invention, or the composition of the invention, will tell the skilled artisan if the agent is effective.

In some embodiments, the therapeutically effective amount is a substantially single-cell therapeutically effective amount. In some embodiments, the single-cell therapeutically effective amount is the single-cell lethal amount.

As used herein, a "single-cell lethal amount" refers to an amount effective, at dosages and for periods of time necessary, to kill a single cell. The lethal amount of the therapeutic agent will depend on the nature of the disorder or condition, the cells targeted and on the particular agent, and can be determined by standard clinical techniques known to a person skilled in the art. In some embodiments, a "single-cell lethal amount" refers to the minimal effective amount sufficient to kill a single cell. The amount may differ depending on cell type, drug type and/or duration of treatment.

In some embodiments, the single-cell lethal amount of a therapeutic agent is a considerably lower dose of the agent as compared to the effective therapeutic dose (ETD) of the therapeutic agent. In some embodiments, the single-cell lethal amount is at most 10%, 7%, 5%, 3%, 2%, 1%, 0.5%, 0.1%, 0.01%, 0.001% or 0.0001% of the effective therapeutic dose (ETD) of the therapeutic agent. Each possibility represents a separate embodiment of the invention. In some embodiments, the single-cell lethal amount is between 10%, and 0.001%, 5% and 0.001%, 3% and 0.001%, 2%, and 0.001%, 1% and 0.001%, 0.5% and 0.001%, 0.1% and 0.001%, 10%, and 0.01%, 5% and 0.01%, 3% and 0.01%, 2%, and 0.01%, 1% and 0.01%, 0.5% and 0.01%, 0.1% and 0.01%, 10%, and 0.1%, 5% and 0.1%, 3% and 0.1%, 2%, and 0.1%, 1% and 0.1%, 0.5% and 0.1%, 10%, and 0.5%, 5% and 0.5%, 3% and 0.5%, 2%, and 0.5%, 1% and 0.5%, 10%, and 1%, 5% and 1%, 3% and 1%, or 2%, and 1% of the MED. Each possibility represents a separate embodiment of the invention. In some embodiments, the single-cell lethal amount is between 0.1% and 3% of the MED In some embodiments, the concentration of therapeutic agent in each type of carrier is above the single-cell lethal amount, and the concentration of therapeutic agents in each type of carrier need not be substantially equal. In some embodiments, the concentration of therapeutic agent in each type of carrier is above the single-cell lethal amount, and the concentration of therapeutic agents in each type of carrier varies by not more than 1, 2, 3, 5, 7, 10, 15, 20, 25, 30, 35, 40, 45, 50, 55, 60, 65, 70, 75, 80, 85, 90, 95 or 100%. Each possibility represents a separate embodiment of the invention. As demonstrated hereinbelow, equal numbers of carriers are more important than equal relative concentration of the agents, so long as the concentration is about the single-cell lethal dose. In some embodiments, the concentration of therapeutic agents in each type of carrier varies by not more than 1, 2, 3, 5, 7, 10 15 or 20%. Each possibility represents a separate embodiment of the invention. In some embodiments, the concentration of therapeutic agents in each type of carrier varies by not more than 10%. In some embodiments, the concentration of therapeutic agents in each type of carrier varies by not more than 1, 2, 3, 5, 7, 10 15 or 20% or the MED. Each possibility represents a separate embodiment of the invention. In some embodiments, the concentration of therapeutic agents in each type of carrier varies by not more than 1% of the MED.

In another embodiment, wherein the therapeutic agent may react with other components of the composition, in order to provide a lethal amount of the agent per a single cell, an excess amount of the agent is used. For a non-limiting example, Cisplatin may react with barcode DNA, therefore in order to provide a cell with a lethal amount of cisplatin an excess amount may be encapsulated.

In some embodiments, a limited amount of a therapeutic agent may be used. As a non-limiting example, a single copy of *Pseudomonas* toxin is sufficient to kill a single cell.

In another embodiment, the single-cell lethal amount is substantially sufficient for killing a single cell. In another embodiment, the therapeutically effective amount is not more than 50%, 40%, 30, 20% or 10% of the amount sufficient for killing a single cell. Each possibility represents a separate embodiment of the invention.

The terms "lethal" or "lethality" as used herein, refers to any type of cell death that comprises release of DNA from the cell interior to the exterior of the cell. In some embodiments, a lethal amount induces apoptosis or necrosis in a cell. In some embodiments, a lethal amount induces apoptosis in a cell. In some embodiments, a lethal amount induces necrosis in a cell.

In some embodiments, the at least one therapeutic agent cannot cross the membrane of the cell. In such embodiments, the lethal amount may be at higher concentration, e.g., compared to concentration for killing a single cell. Examples of therapeutic agents which cannot cross the cell membrane include, but are not limited to, RNA and hydrophilic drugs.

In some embodiments, the single-cell lethal amount comprises a liposomal drug concentration of less than 10, 7, 5, 3, 2, 1, 0.5, 0.1, 0.05, or 0.01 mg/ml. Each possibility represents a separate embodiment of the invention. In some embodiments, the single-cell lethal amount comprises a liposomal drug concentration of less than 2 mg/ml. In some embodiments, the single-cell lethal amount comprises a liposomal drug concentration of between 10 and 0.1, 10 and 0.05, 10 and 0.01, 7 and 0.1, 7 and 0.05, 7 and 0.01, 5 and 0.1, 5 and 0.05, 5 and 0.01, 3 and 0.1, 3 and 0.05, 3 and 0.01, 2 and 0.1, 2 and 0.05, 2 and 0.01, 1 and 0.1, 1 and 0.05, or 1 and 0.01. Each possibility represents a separate embodiment of the invention.

Barcodes

In one embodiment, the barcode is one or more nucleic acid molecules. Nucleic acid molecules, such as DNA strands, present an unlimited number of barcoding options. As used throughout the invention "barcode", and "DNA barcode", are interchangeable with each other and have the same meaning. The nucleic acid molecule serving as a DNA barcode is a polymer of deoxynucleic acids or ribonucleic acids or both and may be single-stranded or double-stranded, optionally containing synthetic, non-natural or altered nucleotide bases. In some embodiments, the nucleic acid molecule is labeled, for instance, with biotin, a radiolabel, or a fluorescent label.

As will be appreciated by a person skilled in the art, incorporation of unique DNA barcodes into the therapeutic agent carriers (encapsulation) allows the identification of individual therapeutic agents using assays including, but not limited to, microarray systems, PCR, nucleic acid hybridization (including "blotting") or high throughput sequencing.

In some embodiments, penetration of a negatively charged DNA barcode through the negatively charged lipid bilayer of a cell is enabled by encapsulation of the DNA barcode within a carrier.

In some embodiments, the sequence of the nucleic acid molecule is exclusive of sequences, patterns, signatures or any other nucleic acid sequences associated with a material/substance/particle that is naturally occurring in the environment or particularly naturally occurring in the cell being targeted by the methods of the invention. In additional embodiments, the sequence of the nucleic acid molecule is devoid of nucleotide sequences of more than 10 bases which can associate with a naturally occurring nucleotide sequence, and particularly of an exon. In another embodiment, the nucleic acid molecule comprises a sequence which is not substantially identical or complementary to the cell's genomic material (such as to prevent hybridization of the nucleic acid molecule with the cell's genomic material, particularly of the cell's exons and/or prevent false positive amplification results).

In some embodiments, the nucleic acid sequence may further serve as a molecular beacon. The nucleic acid sequence may typically be a single strand molecule such as a hairpin. The nucleic acid molecule may be used for detecting a complementary gene in the cell, such as for the detection of a genetic mutation inside the cell. In some embodiments, the nucleic acid has a sequence complementary to a mutation bearing sequence.

In some embodiments, the nucleic acid molecule comprises or consists of a pre-defined unique sequence. As used herein, the term "unique sequence" or "uniquely identifying" refers to a sequence based on an injective function (also termed one-to-one function) that preserves distinctness.

A unique barcode (e.g., a nucleic acid having a unique sequence) is suitable for identifying the corresponding at least one therapeutic agent within the carrier after implementing the methods of the invention. Methods for the detection of the presence and identification of a nucleic acid sequence are known to a skilled artisan and include sequencing and array (e.g., microarray) systems capable of enhancing the presence of multiple barcodes (e.g., commercially available by Ilumina Inc.).

In some embodiments, such as where increased accuracy is desirable, the nucleic acid molecule has a length suitable for sequencing and/or amplification assays (e.g. PCR). In another embodiment, the nucleic acid molecule has a length suitable for loading into the carriers of the invention, preferably in the nanoscale. It should be appreciated that the length of the nucleic acid molecule is dependent on the type and size of the carrier used in the compositions and methods of the invention (e.g., shorter sequences are suitable for use in nanoparticles whereas longer sequences may be used in microparticles).

In another embodiment, the nucleic acid molecule has a length of at most 1000, at most 900, at most 800, at most 700, at most 600, at most 500, at most 450, at most 400, at most 350, at most 300, at most 250, at most 200, at most 190, at most 180, at most 170, at most 160, at most 150, at most 140, at most 130 or at most 120 bases, wherein each possibility represents a separate embodiment of the present invention. In another embodiment, the nucleic acid molecule has a length of at least 5, at least 6, at least 7, at least 8, at least 9, at least 10, at least 11, at least 12, at least 13, at least 14, at least 15, at least 16, at least 17, at least 18, at least 19 or at least 20 bases, at least 21, at least 22, at least 23, at least 24, at least 25, at least 26, at least 27, at least 28, at least 29 or at least 30 bases, at least 40, at least 50, at least 60, at least 70, at least 80, at least 90, at least 100 or at least 200, at least 300, at least 400 or at least 500 bases, wherein each possibility represents a separate embodiment of the present invention.

Non-limiting examples of nucleic acid lengths include, but are not limited to, 5-50 bases, 5-40 bases, 5-30 bases, 5-25 bases, 5-24 bases, 5-23 bases, 5-22 bases, 5-21 bases, 5-20 bases, 5-19 bases, 5-18 bases, 5-17 bases, 5-16 bases or 5-15 bases, 15-50 bases, 15-60 bases, 15-70 bases, 15-80 bases, 15-90 bases, 15-100 bases, 15-200 bases, 15-250 bases or 15-500 bases.

In another embodiment, the nucleic acid molecule within each carrier has a concentration of one or more strands per carrier or per targeted cell. Determining the amount of the nucleic acid molecule is well within the capability of a person skilled in the art. In another embodiment, the one or more nucleic acid molecules is 1-10000 nucleic acid molecules. In another embodiment, the one or more nucleic acid molecules is 1-1000 nucleic acid molecules. In another embodiment, the one or more nucleic acid molecules is 1-5000 nucleic acid molecules. In another embodiment, the one or more nucleic acid molecules is 1-500 nucleic acid molecules. In another embodiment, the one or more nucleic acid molecules is 5-500 nucleic acid molecules. One skilled in the art will appreciate that the quantity of nucleic acid molecules in each particle may be pre-determined so as to suit the specific assay performed, e.g., sequencing and/or amplification assays.

According to some embodiments, each particle comprises a unique barcode. One skilled in the art will appreciate that bar-coding each particle (i.e., carrier) with a unique barcode may indicate the number of particles that entered a single cell. In some embodiments, the invention provides a method of determining a therapeutic dose for treating a disease, the method comprises administering to a subject a composition comprising a plurality of types of carries, wherein each type of carrier comprises one or more therapeutic agents, wherein each type of carrier differs in the dose of the one or more therapeutic agents.

According to some embodiments, each type of particle (i.e., carrier) comprises a unique barcode (e.g., nucleic acid sequence) identifying the type of carrier. According to some embodiments, each particle (i.e., carrier) comprises a unique barcode (e.g., nucleic acid sequence) identifying the type of carrier.

In another embodiment, the barcode is selected from the group consisting of: a rare earth element, a fluorophore, a chromophore, a chemiluminescent molecule, a magnetic particle, a dye, and a radioactive isotope.

In another embodiment, the barcode is a rare earth element. In another embodiment, the rare earth element is a lanthanide. In some embodiments, the lanthanide is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), Scandium (Sc) and yttrium (Y). In some embodiments, the lanthanide is selected from La, Ce, Pr, Nd, Pm, Sm, Eu, Gd, Tb, Dy, Ho, Er, Tm, Yb and Lu.

The rare earth elements (e.g., lanthanides) may be useful when complexed with a luminescence label and are generally utilized by combining a lanthanide complex with the sample of interest under conditions selected to yield a detectable optical response. The sample may be illuminated at a wavelength selected to elicit an optical response.

In another embodiment, the carrier within the composition further comprises additional agents (e.g. chemical or biological agent) for operably using the nucleic acid molecule as a barcode in a cell. Non-limiting examples of the agents include DNase or RNase inhibitors, such as to prevent degradation by endogenous or exogenous enzymes of the DNA or RNA barcode, respectively.

In some embodiments, the barcode concentration in the solution forming the composition can vary between 0.001 to 100, 0.005 to 100, 0.01 to 100, 0.05 to 100, 0.1 to 100, 0.5 to 100, 1 to 100, 2 to 100, 5 to 100, 10 to 100, 15 to 100, 20 to 100, 25 to 100, 30 to 100, 0.001 to 90, 0.005 to 90, 0.01 to 90, 0.05 to 90, 0.1 to 90, 0.5 to 90, 1 to 90, 2 to 90, 5 to 90, 10 to 90, 15 to 90, 20 to 90, 25 to 90, 30 to 90, 0.001 to 80, 0.005 to 80, 0.01 to 80, 0.05 to 80, 0.1 to 80, 0.5 to 80, 1 to 80, 2 to 80, 5 to 80, 10 to 80, 15 to 80, 20 to 80, 25 to 80, 30 to 80, 0.001 to 70, 0.005 to 70, 0.01 to 70, 0.05 to 70, 0.1 to 70, 0.5 to 70, 1 to 70, 2 to 70, 5 to 70, 10 to 70, 15 to 70, 20 to 70, 25 to 70, or 30 to 70 micromols/liter (µM). Each possibility represents a separate embodiment of the invention. In some embodiments, the barcode concentration in the solution can vary between 2 to 100 micromols/liter (µM). In some embodiments, the barcode concentration in the solution can vary between 10 to 90 micromols/liter (µM). In some embodiments, the barcode concentration in the solution can vary between 20 to 80 micromols/liter (µM). In some embodiments, the barcode concentration in the solution can vary between 30 to 70 micromols/liter (µM).

In some embodiments, each type of carrier comprises a substantially equal barcode concentration. In some embodiments, each type of carrier comprises an equal barcode concentration. In some embodiments, the barcode concentration in the types of barcodes varies by not more than 0.1, 0.5, 1, 2, 3, 5, 7, 10, 15, 20 or 25%. Each possibility represents a separate embodiment of the invention.

In one embodiment, the composition described herein comprises a small number of nanoparticles, relative to the quantity of analyzed cells, so as to ensure the statistical significance of the data. In some embodiments, the number of barcoded nanoparticles per cell of the disease, is preferably less than 5. The invention is based in part on the finding that the number of particles that should be injected in order to achieve a presence of up to 5 barcode types per disease cell may be calculated by taking into account that 6-7% of an intravenously injected dose accumulates at a tumor site and 5% of the nanoparticles that actually reach the tumor site are taken up by cells, while the rest are trapped in the extracellular matrix (ECM).

In one embodiment, 1-5 types of carriers (i.e., barcoded nanoparticles) are present per disease cell. In another embodiment, the presence of 1-5 types of carriers per disease cell provides sufficient data and high signal to noise ratio (SNR) when analyzing bodily fluid. As used herein, "fluid" and "bodily fluid" are interchangeable.

In one embodiment, 1-200 particles or particles of each type per tumor cell are administered via intravenous injection. In another embodiment, 1-300 particles or particles of each type per tumor cell are administered via intravenous injection. In another embodiment, 1-400 particles or particles of each type per tumor cell are administered via intravenous injection. In another embodiment, 1-500 particles or particles of each type per tumor cell are administered via intravenous injection. In another embodiment, 1-1000 particles or particles of each type per tumor cell are administered via intravenous injection.

In another embodiment, 1-20 particles or particles of each type per tumor cell are administered intratumorally. In another embodiment, 1-10 particles or particles of each type per tumor cell are administered intratumorally. In another embodiment, 1-50 particles or particles of each type per tumor cell are administered intratumorally. In another embodiment, 1-100 particles or particles of each type per tumor cell are administered intratumorally.

In some embodiments, the amount of barcode molecules inside the particle is at least 1, or alternatively at least 5, or alternatively at least 10, or alternatively at least 20, or alternatively at least 30, or alternatively at least 40, or alternatively at least 50, or alternatively at least 60, or alternatively at least 70, or alternatively at least 80, or alternatively at least 90, or alternatively at least 100, or alternatively at least 500, or alternatively at least 1000, or alternatively at least 5000, or alternatively at least 10000 barcode molecules/particle. Each possibility represents a separate embodiment of the invention. In some embodiments, the amount of barcode molecules inside the particle is at most 5, or alternatively at most 10, or alternatively at most 20, or alternatively at most 30, or alternatively at most 40, or alternatively at most 50, or alternatively at most 60, or alternatively at most 70, or alternatively at most 80, or alternatively at most 90, or alternatively at most 100, or alternatively at most 500, or alternatively at most 1000, or alternatively at most 5000 barcode molecules/particle. Each possibility represents a separate embodiment of the invention. In some embodiments, the amount of barcode molecules inside the particle ranges between 5-100 barcode molecules/particle. In some embodiments, the amount of barcode molecules inside the particle ranges between 10-90 barcode molecules/particle. In some embodiments, the amount of barcode molecules inside the particle ranges between 20-80 barcode molecules/particle. Each possibility represents a separate embodiment of the invention. In some embodiments, the amount of barcode molecules inside the particle ranges between 1-1000 barcode molecules/particle. In some embodiments, the amount of barcode molecules inside the particle ranges between 1-10000 barcode molecules/particle.

Cleavage Sites

In some embodiments, the unique barcode comprises at least one cleavage site. In some embodiments, the unique barcode comprises a plurality of cleavage sites. As used herein, a cleavage site refers to a nucleotide sequence which can be cleaved or cut by a sequence-specific or structure-specific nuclease. Design of DNA and RNA molecules with cleavage sites for either sequence-specific or structure-specific nucleases is routine for one skilled in the art, and it will be understood that single-stranded, double-stranded, nicked, mismatched, or in any other way unique nucleotide structures or sequences may be employed for this purpose. In some embodiments, the cleavage site is specifically cut by a nuclease specific to a cell of the disease. Such a nuclease, for example, could be a tumor-specific nuclease, or a stem cell-specific nuclease.

In some embodiments, the cleavage site is specifically cut by a nuclease that is mislocalized to the cytoplasm in a cell of the disease. In some embodiments, the cleavage site is specific to a nuclease with increased cytoplasmic localization in a cell of the disease. Many nucleases have exclusive, or near-exclusive nuclear staining in healthy cells. In embodiments in which the barcode lacks a nuclear localization or nuclear import signal, a barcode with a cleavage site would not be cleaved or would be lowly cleaved in healthy cells where interaction between the cytoplasmic barcode and the nuclear nuclease would be limited. In disease cells in which a nuclease is mislocalized to, or overexpressed in, the cytoplasm the barcode and nuclease would be free to interact resulting in cleavage.

Nucleases, such as DNA2 as a non-limiting example, are known to be overexpressed in many cancers, including breast and pancreas cancers, and overexpression can lead to cytoplasmic leakage. Non-limiting examples of nucleases mislocalized to the cytoplasm in disease cells include human apurinic/apyrimidinic endonuclease APE1, which has been shown to have cytoplasmic localization in breast cancers, rectal cancers, ovarian cancers, thyroid carcinomas and non-small cell lung cancers and XPF-ERCC1 which has been shown to have cytoplasmic localization in xeroderma pigmentosum cells. In some embodiments, the unique barcode comprises an APE1 cleavage site.

A skilled artisan will understand that measurement of cleaved versus uncleaved barcodes within a sample from a subject would thus allow for measuring the efficacy of a therapeutic agent specifically in cells of the disease. Distinguishing between cleaved and uncleaved nucleotide sequences can be achieved though routine nucleotide detection/identification assays such as have been described herein above.

Tags

In another embodiment, the one or more carriers of the invention further comprise at least one tag or detectable moiety. In some embodiments, an identical tag is used for all carriers. In other embodiments, a unique tag is used for a sub-set of carriers.

Tags which may be used in the compositions and methods of the invention include but are not limited to a fluorophore, a chromophore, a chemiluminescent molecule, a radiomarker, a metal, a rare earth, magnetic particle or a dye.

In some embodiments, the tag or detectable moiety is a tag useful in assays including but not limited to immunological assay such as ELISA, bead-, chip- or plate-based multiplex immunoassays, mass spectrometry, electrophoresis, immunonephelometry, immunoturbidimetry, enzymatic assays, colorimetric or fluorometric assays e.g. evaluable by photometry, and fluorescence-associated cell sorting (FACS)-based analyses or by other clinically established assays. All these methods are well known to the person of skill in the art and described in the literature.

Typically, the amount of the tag will depend on the assay to be performed and can be determined by and is well under the capability of a person skilled in the art. In some embodiments, the carrier comprises one molecule or more molecules of said tag.

In some embodiments, the tag is encapsulated inside the carrier. In some embodiments, the tag is anchored to the outside of the carrier. In some embodiments, the tag is anchored in the membrane of the carrier. In some embodiments, the tag is anchored to or in the carrier via a linker. Such a linker may be, but is not limited to an amino acid, a lipid, a carbohydrate or a combination thereof.

Carriers

In some embodiments, there is provided carriers for therapeutic agent(s), nucleic acid sequences useful for DNA barcoding said therapeutic agent(s) and optionally a tag. Said carrier used to practice the methods of the invention may target specific molecules, including biologic molecules, such as polypeptide, including cell surface polypeptides, e.g., polypeptides on abnormally growing cells, cancer cells, immune cells and degenerative cells.

In alternative embodiments, the invention provides carriers in the form of nanoparticles and liposomal membranes comprising (in addition to comprising compounds used to practice the methods of the invention) molecules, e.g., peptides or antibodies, that selectively target abnormally growing, diseased, infected, dysfunctional and/or cell receptors.

In some embodiments, said at least one carrier is in the form of a vesicle such that carried materials (therapeutic agent, nucleic acid molecule and optionally a tag) are inside an internal core. In some embodiments, said at least one carrier is a lipid-based particle. In another embodiment, said lipid-based particle is a liposome. In another embodiment, said at least one carrier is a micelle.

In some embodiments, the solution is inert to and does not affect the designated cell. In some embodiments, all components of the composition, besides the therapeutic agent, are inert and do not affect the designated cell. In some embodiments, the solution is an aqueous solution. In another embodiment, the composition of the invention is devoid of a cationic surfactant (as it may affect a cell and/or affect the activity of the therapeutic agent and prevent accurate analysis of the effect of the therapeutic agent).

In some embodiments, said at least one carrier is in the form of a vesicle such that carried materials (therapeutic agent, nucleic acid molecule and optionally a tag) form a complex/particulate with the carried materials with or without another agent such as a polymer/protein/salt. In some embodiments, said at least one carrier forms a dendrimer like structure in which the components are conjugated to the polymeric backbone or complexed via van der Waals or hydrophobic interactions.

In some embodiments, said at least one carrier is a polymeric nanoparticle. In some embodiments, said at least one carrier is a nanogel. In some embodiments, said at least one carrier is a metallic nanoparticle (e.g., a gold or iron oxide nanoparticle). In some embodiments, said at least one carrier is carbon nanotube. In some embodiments, said at least one carrier is a layer by layer particle. In some embodiments, said at least one carrier is a sol-gel ceramic particle. In some embodiments, said at least one carrier is a protein complex with the drug.

In some embodiments, said at least one carrier forms a dendrimer like structure in which the components are conjugated to the polymeric backbone or complexed via van der Waals or hydrophobic interactions.

In one embodiment, the carrier (e.g., liposome) is less than 500 nm in diameter to facilitate its entrance through the extracellular matrix to a cell. In one embodiment, the carrier (e.g., liposome) is less than 400 nm in diameter to facilitate its entrance through the extracellular matrix to a cell.

In one embodiment, the carrier (e.g., liposome) is less than 300 nm in diameter, less than 250 nm, less than 200 nm in diameter, less than 150 nm in diameter, less than 100 nm in diameter, less than 50 nm in diameter, less than 20 nm in diameter, less than 10 nm in diameter or less than 5 nm in diameter. In another embodiment, the carrier (e.g., liposome) is at least 1 nm in diameter, at least 5 nm in diameter, at least 10 nm in diameter, at least 20 nm in diameter, at least 30 nm in diameter, at least 40 nm in diameter, at least 50 nm in diameter, at least 60 nm in diameter, at least 70 nm in diameter, at least 80 nm in diameter, at least 90 nm in diameter, at least 100 nm in diameter, at least 150 nm in diameter, at least 200 nm in diameter, at least 250 nm in diameter or at least 300 nm in diameter. Each possibility represents a separate embodiment of the invention.

In another embodiment, the carrier is 1-300 nm in diameter. In another embodiment, the carrier is 10-250 nm in diameter. In another embodiment, the carrier is 5-250 nm in diameter. In another embodiment, the liposome is 20-150 nm in diameter. In another embodiment, the liposome is 5-150 nm in diameter. In another embodiment, the liposome is 20-150 nm in diameter.

In some embodiments, a carrier for intravenous administration is 5-250 nm in diameter. In some embodiments, wherein the carrier for intravenous administration is a liposome, the carrier is 40-250 nm in diameter. In some embodiments, a carrier for intratumoral administration is 5-300 nm in diameter. In some embodiments, wherein the carrier for intratumoral administration is a liposome, the carrier is 40-300 nm in diameter.

In some embodiments, the morphology of the carrier may be spherical or substantially spherical, non-spherical (e.g. elliptical, tubular, etc.), irregular etc.

The use of liposomal transfer vehicles to facilitate the delivery of therapeutic agents and nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, ibid.). Bilayer membranes of the liposomes can also be formed by amphiphilic polymers and surfactants (e.g., polymerosomes, niosomes, etc.).

In one embodiment, the carrier may be selected and/or prepared to optimize delivery of the therapeutic agent and nucleic acid molecule (the DNA barcode) to a target cell. For example, if the target cell is a hepatocyte the properties of the transfer vehicle (e.g., size, charge and/or pH) may be optimized to effectively deliver such transfer vehicle to the target cell. Alternatively, if the target cell is the central nervous system (e.g., for therapy predication of neurodegenerative diseases), selection and preparation of the transfer vehicle must consider penetration of, and retention within the blood brain barrier and/or the use of alternate means of directly delivering such transfer vehicle to such target cell.

The process of incorporation of a desired entity into a liposome is often referred to as "loading" (Lasic, et al., FEBS Lett., 312: 255-258, 1992). The liposome-incorporated therapeutic agents, nucleic acids and/or tag, may be completely or partially located in the interior space of the liposome, within the bilayer membrane of the liposome. Incorporation of an agent into liposomes is also referred to herein as "encapsulation" wherein the agent is entirely contained within the interior space of the liposome. Typically, for encapsulation of an agent within a carrier (e.g. liposome) a chemical linkage, such as a covalent linkage between the agent and the carrier, is not required. The purpose of incorporating an agent into a transfer vehicle, such as a liposome, is often to protect the agent from an environment which may contain enzymes or chemicals that degrade the agent (e.g., nucleic acids) and/or systems or receptors that cause the rapid excretion of the agent. Accordingly, in a preferred embodiment of the present invention, the selected transfer vehicle is capable of enhancing the stability of the therapeutic agent and the nucleic acid molecule and optionally the tag contained therein. The liposome can allow the encapsulated agents to reach the target cell and/or may preferentially allow the encapsulated agents to reach the target cell, or alternatively limit the delivery of the agents to other undesired target sites or cells.

In some embodiments, the carrier facilitates penetration of the encapsulated therapeutically effective amount of at least one therapeutic agent, the nucleic acid molecule uniquely identifying the at least one therapeutic agent and the optional tag to a cell. In some embodiments, the penetration of therapeutically effective amount of at least one therapeutic agent, the nucleic acid molecule uniquely identifying the at least one therapeutic agent and the optional tag to a cell is enabled by encapsulation within a carrier.

In some embodiments, liposomal transfer vehicles are prepared to encapsulate one or more desired agent such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28-fold in a number of cell lines both in vitro and in vivo. (See N. J. Caplen, et al., Gene Ther. 1995; 2: 603; S. Li, et al., Gene Ther. 1997; 4, 891).

In another embodiment, said at least one carrier is a nanoliposome or lipid nanoparticle. Nanoliposomes are able to enhance the performance of bioactive agents by improving their solubility and bioavailability, in vitro and in vivo stability, as well as preventing their unwanted interactions with other molecules. Another advantage of nanoliposomes is cell-specific targeting, which is a prerequisite to attain drug concentrations required for optimum lethality in the target cell while minimizing adverse effects on healthy cells and tissues. In some embodiments, the at least one carrier is a liposome.

As used herein, the phrase "lipid nanoparticle" refers to a transfer vehicle comprising one or more lipids (e.g., cationic lipids, non-cationic lipids, and PEG-modified lipids). Preferably, the lipid nanoparticles are formulated to deliver one or more agents to one or more target cells. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a nucleic acid to a target cell.

The invention contemplates the use of lipid nanoparticles as transfer vehicles comprising a cationic lipid to encapsulate and/or enhance the delivery of nucleic acid into the target cell. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids for use in the compositions and methods of the invention include those described in international patent publication WO 2010/053572, incorporated herein by reference in its entirety. In certain embodiments, the compositions and methods of the invention employ a lipid nanoparticle comprising an ionizable cationic lipid. In some embodiments, the cationic lipid N-[1-(2,3-dioleyloxy)propyl]-N,N,N-trimethylammonium chloride or "DOTMA" is used. (U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethyl-ammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-b eta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl[1,3]-dioxolane or "DLin-K-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-di-methylethanamine (DLin-KC2-DMA)) (See, WO 2010/042877; Semple et al., Nature Biotech. 28:172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE 2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle. Each possibility represents a separate embodiment of the invention.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, hydrogenated soy phosphatidylcholine (HSPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In some embodiments, the transfer vehicle (e.g., a lipid nanoparticle) is prepared by combining multiple lipid and/or polymer components. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells and the characteristics of the agents to be delivered. Additional considerations include, for example, the saturation of the alkyl chain, as well as the size, charge, pH, pKa, fusogenicity and toxicity of the selected lipid(s).

The liposomal transfer vehicles for use in the compositions of the invention can be prepared by various techniques which are presently known in the art. Multi-lamellar vesicles (MLV) may be prepared by conventional techniques, for example, but not limited to, by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the compositions of the invention may be loaded with diagnostic radionuclide, fluorescent materials or other materials that are detectable in both in vitro and in vivo applications.

In some embodiments, the nanoparticle carriers of the invention are fabricated of lipids using an in-line microfluidic setup adapted to accommodate high-throughput synthesis and labeling of the particles. Such fabrication methods are known in the art, e.g., Jahn et al., 2007, Langmuir 23, 6289-6293. Typically, particles of appropriate sizes to accommodate the therapeutic payload are fabricated.

Chemical agents may be loaded into stable HSPC particles, for examples as shown by Schroeder et al., 2007, Langmuir 23, 4019-4025. Biological therapeutics (protein/RNA) may be synthesized inside 'protein producing nanoparticles'. In some embodiments, a synthetic nanoparticle is controllably triggered to synthesize proteins and RNA at a target site, as shown in Schroeder, A. et al. *Nano Lett* 12, 2685-2689, (2012). These nanoparticles consist of lipid vesicles filled with the molecular machinery responsible for transcription and translation, including amino acids, ribosomes, and DNA caged with a photo-labile protecting group. The particles serve as nano-factories capable of producing RNA/proteins. In vitro and in vivo, protein/RNA synthesis may be spatially and temporally controllable, and can be initiated by illuminating micron-scale tissue regions on the timescale of milliseconds. As such, this platform may be used to screen RNA (Png et al. 2012 Nature 481, 190-194) and proteins for their activity, e.g., anti-cancer activity.

In some embodiments, the nanoparticle (e.g., carrier) of the invention is a nanoparticle wherein the liposome-forming lipid constitutes 40-100% mol of the nanoparticle. In some embodiments, the nanoparticle of the invention comprises 0-50% % mol cholesterol. In some embodiments, the nanoparticle of the invention comprises 1-8% mol PEG-lipid. In some embodiments, the nanoparticle of the invention comprises 0-10% mol of a functional lipid (e.g., a cationic lipid or a lipid with a targeting moiety).

As used herein and in the art, mol percent ("% mol") refers to a percent of a particular component or compound based on the total mols of the components or compounds constituting the nanoparticle. For example, if a nanoparticle contains three mols of compound A and one mol of compound B, then the compound A comprises 75 mol % of the mixture and the compound B comprises 25 mol %.

In some embodiments, the nanoparticle (e.g., carrier) of the invention comprises 40-70% mol liposome-forming lipid. In some embodiments, the nanoparticle of the invention comprises 20-50% mol cholesterol. In some embodiments, the nanoparticle of the invention comprises 4-8% mol PEG-lipid. In some embodiments, the nanoparticle of the invention comprises 0-3% mol of a functional lipid (e.g., a cationic lipid or a lipid with a targeting moiety). According to specific embodiment, a nanoparticle comprising 40-70% mol liposome-forming lipid, 20-50% mol cholesterol, 4-8% mol PEG-lipid and 0-3% mol of a functional lipid is suitable for intravenous administration.

In some embodiments, the nanoparticle (e.g., carrier) of the invention comprises 50-80% mol liposome-forming lipid. In some embodiments, the nanoparticle of the invention comprises 0-50% mol cholesterol. In some embodiments, the nanoparticle of the invention comprises 0-3% mol PEG-lipid. In some embodiments, the nanoparticle of the invention comprises 4-8% mol of a functional lipid (e.g., a cationic lipid or a lipid with a targeting moiety). According to specific embodiment, a nanoparticle comprising 50-80 mol liposome-forming lipid, 0-50% mol cholesterol, 0-3% mol PEG-lipid and 4-8% mol of a functional lipid is suitable for intratumoral administration.

Theranostic Use

By one aspect, the present invention provides a method for predicting the response of a subject afflicted with a disease to at least one therapeutic agent, the method comprising the steps of:
(a) administering to the subject a composition comprising a plurality of types of carriers, each type of carrier independently comprises at least a single-cell therapeutically effective amount of at least one therapeutic agent and one or more barcodes uniquely identifying the at least one therapeutic agent;
(b) obtaining a fluid sample from the subject; and
(c) identifying, in the fluid, the efficacy of the at least one therapeutic agent by the presence of the unique barcode;
thereby predicting the response of a subject afflicted with a disease to a therapeutic agent.

By another aspect, the present invention provides a method for predicting the response of a subject afflicted with a disease to at least one therapeutic agent, the method comprising the steps of:
(a) administering to the subject a composition comprising a plurality of types of carriers, each type of carrier independently comprises at least a single-cell therapeutically effective amount of at least one therapeutic agent and one or more barcodes uniquely identifying the at least one therapeutic agent;
(b) obtaining a fluid sample from the subject; and
(c) determining if a unique barcode is present in the fluid, wherein presence of the unique barcode indicates the subject responds to the therapeutic agent;
thereby predicting the response of a subject afflicted with a disease to a therapeutic agent.

In another embodiment, the method further comprises a step of sequencing the nucleic acid molecule. In another embodiment, the method further comprises a step of amplifying the nucleic acid molecule. As used herein, the terms "identifying" and "determining" are used interchangeable, and refer to ascertaining if a barcode is present in the fluid. In some embodiments, the identifying comprises sequencing and/or amplifying the nucleic acid molecule. Methods for amplifying and sequencing nucleic acids are well known to a person skilled in the art.

In another embodiment, the method further comprises removing intact cells from the fluid sample before step (c). Removal of intact cells will be well known to a skilled artisan and can include, but is not limited to, differential centrifugation, filtering, immuno-selective beads or sorting. In some embodiments, the method further comprises counting the intact cells. In some embodiments, the method further comprises detecting at least one barcode in the intact cells. In embodiments wherein the barcodes from intact cells are detected, identifying the efficacy of the at least one therapeutic agent by the unique barcode comprises a comparison to the barcode levels in intact cells. In some embodiments, identifying the efficacy of the at least one therapeutic agent comprises detecting extracellular barcodes in the bodily fluid.

In some embodiments, the method further comprises removing intact carriers from the bodily fluid before step (c). In another embodiment, the at least one carrier is a liposome and the method further comprises removing intact liposomes or nanoliposomes from the fluid sample before step (c). A non-limiting example of a method for removal of intact liposomes is differential centrifugation. In some embodiments, the method further comprises counting the number of intact liposomes. In some embodiments, the method further comprises detecting at least one barcode in the intact liposomes. In embodiments wherein the barcodes from intact liposomes are detected, identifying the efficacy of the at least one therapeutic agent by the unique barcode comprises a comparison to the barcode levels in intact liposomes. In some embodiments, the liposomes are nanoliposomes. In some embodiments, identifying the efficacy of the at least one therapeutic agent comprises detecting extra-liposomal or extra-carrier barcodes in the bodily fluid.

In some embodiments, the administered composition is the composition of the invention. In some embodiments, the administered composition is a composition with substantially equal numbers of each type of carrier.

In another embodiment, the method further comprises before step (a) obtaining a fluid sample from the subject and identifying the percentage of circulating tumor DNA in the sample. Circulating tumor DNA is well known in the art as are methods of identifying such. In some embodiments, tumor DNA is identified by the presence of driver mutations or small nucleotide variations (SNVs). Driver mutations can be detected using methods of nucleotide detection described herein above, and specifically but non-limiting with the Ion Ampliseq Comprehensive Cancer Panel (Life Technologies). In embodiments, wherein the percentage of tumor DNA in a sample is identified, identifying the efficacy of the at least one therapeutic agent by the unique barcode comprises a comparison to the pre-administration tumor DNA percentage. In some embodiments, the comparison enables distinguishing if a barcode in the sample comes from killing healthy cells or killing cells of the disease. In some embodiments, the method further comprises identifying the percentage of tumor DNA in the fluid as part of step (c).

In another embodiment, the method further comprises a washing and DNAse treatment step, following incubation of the agents with the target cells.

As used herein the terms "fluid" and "bodily fluid" are used interchangeable and refer to any fluid produced by the body of a subject. In some embodiments, the fluid is selected from the group consisting of: blood, serum, plasma, saliva, urine, lymph, tumor fluid, breast milk, cerebral spinal fluid and seminal fluid. In some embodiments, the fluid is blood. Withdrawal of bodily fluids will be routine to one skilled in the art. The bodily fluid obtained will be selected as necessitated by the disease, as for example cerebral spinal fluid may be obtained for a brain tumor, lymph may be obtained for a metastatic cancer, breast milk may be obtained for a breast tumor or seminal fluid may be obtained for a prostate cancer to name but a few possible fluids and diseases. A skilled artisan will be able to determine the proper fluid to be obtained, though withdrawal of blood may be employed for most diseases. Fluid from around or close to the tumor, herein referred to as "tumor fluid" may also be obtained for solid tumors, such as malignant cysts for which removal of cyst fluid is routine.

In some embodiments, the amount of fluid obtained is an amount sufficient for extracting sufficient barcodes as to provide statistically significant data. In some embodiments, the amount of fluid obtained is sufficient for performing deep sequencing of barcodes. In some embodiments, the amount of fluid obtained is sufficient for PCR or other forms of nucleotide amplification. In some embodiments, the amount of fluid obtained is at least 1, 2, 3, 4, 5, 6, 7, 8, 9, 10, 11, 12, 13, 14, or 15 milliliters (mLs). Each possibility represents a separate embodiment of the invention. In some embodiments, 1-5, 1-10, 1-15, 5-10, or 5-15 mLs are obtained. Each possibility represents a separate embodiment of the invention.

In some embodiments, nucleic acids are isolated from the fluid before identification of barcodes. In some embodiments, identification is performed in the unaltered fluid. In some embodiments, the fluid is processed before nucleic acids are isolated or identification is performed. In some embodiments, the fluid processing comprises removal of intact cells and/or carriers. In some embodiments, the processing comprises separating components from the fluid. In some embodiments, the fluid is blood and the processing comprises separation of plasmid. In some embodiments, DNA and RNA are separated before identification of barcodes. Nucleic acid isolation, and identification is well known in the art and may employ differential centrifugation, precipitation or selective enzymatic digestion for example.

In some embodiments, the methods disclosed herein include providing sufficient amounts of time for the therapeutic agent to kill cells. In some embodiments, the methods disclosed herein include providing sufficient amounts of time for free intact carriers to substantially clear from the bodily fluid. The time required for intact carriers to clear will depend on the initial number of carriers introduced. Sufficient time may be determined empirically by testing blood at intervals after administration. The sufficient amount of time before sampling a bodily fluid will depend on the nature of the disorder or condition and on the particular agent and can be determined by standard clinical techniques known to a person skilled in the art. As non-limiting examples, sufficient amounts of time include about 24, about 30, about 48, about 72, about 96, about 120, about 144, about 168, about 192 hours or more. Each possibility represents a separate embodiment of the invention. In some embodiments, in order to avoid degradation of the barcode inside the bodily fluid the sustained amount of time is less than 144 hours.

In some embodiments, the obtaining is performed within a time frame of 3-240, 12-240, 24-240, 48-240, 72-240, 96-240, 3-192, 12-192, 24-192, 48-192, 72-192, 96-192, 3-144, 12-144, 24-144, 48-144, 72-144 or 96-144 hours. Each possibility represents a separate embodiment of the invention. In some embodiments, the obtaining is performed after 24, 48, 72, 96, 120, 144, 168, 192, 216 or 240 hours. Each possibility represents a separate embodiment of the invention.

In some embodiments, the sustained amount of time before sampling the targeted cells ranges from 24 to 72 hours. In some embodiments, the sustained amounts of time before sampling the targeted cells range from 24 to 96 hours. In other embodiments, the sustained amounts of time before sampling the targeted cells range from 24-120 hours. In other embodiments, the sustained amounts of time before sampling the targeted cells range from 24-144 hours. In other embodiments, the sustained amounts of time before sampling the targeted cells range from 24-192 hours. In some embodiments, the sustained amount of time before sampling the targeted cells ranges from 48 to 72 hours. In some embodiments, the sustained amounts of time before sampling the targeted cells range from 48 to 96 hours. In other embodiments, the sustained amounts of time before sampling the targeted cells range from 48-120 hours. In other embodiments, the sustained amounts of time before sampling the targeted cells range from 48-144 hours. In other embodiments, the sustained amounts of time before sampling the targeted cells range from 48-192 hours. In other embodiments, the sample is obtained at least 24 hours following administration of the composition. In other embodiments, the sample is obtained at least 48 hours following administration of the composition. In other embodiments, the sample is obtained at least 72 hours following administration of the composition. In other embodiments, the sample is obtained at least 96 hours following administration of the composition. In other embodiments, the sample is obtained at least 144 hours following administration of the composition. In other embodiments, the sample is obtained at most 48 hours following administration of the composition. In other embodiments, the sample is obtained at most 72 hours following administration of the composition. In other embodiments, the sample is obtained at most 96 hours following administration of the composition. In other embodiments, the sample is obtained at most 120 hours following administration of the composition. In other embodiments, the sample is obtained at most 144 hours following administration of the composition. In other embodiments, the sample is obtained at most 192 hours following administration of the composition. In other embodiments, the sample is obtained at most 240 hours following administration of the composition. In other embodiments, the sample is obtained between 24-192 hours following administration of the composition. In other embodiments, the sample is obtained between 48-192 hours following administration of the composition. In other embodiments, the sample is obtained between 24-240 hours following administration of the composition. In other embodiments, the sample is obtained between 48-240 hours following administration of the composition. The exact time frame for sampling the targeted cells may be determined according several factors, including the type and amount of barcode used and the therapeutic agent being examined. As a non-limiting example, nucleic acid molecules are typically susceptible to degradation 48 hours following administration (particularly systemic administration) whereas rare earth elements can be detected for longer periods of time. In other embodiments, therapeutic agents differ by the time they act on a target cell.

In some embodiments, the therapeutic agent (e.g., cisplatin) comprises a unique barcode. One skilled in the art will appreciate that in such embodiments, said carrier may comprise the therapeutic agent (e.g., cisplatin) and there is no need to add an additional barcode.

In another embodiment, said composition is formulated for systemic administration. In another embodiment, said systemic administration is intravenous injection. In another embodiment, said administration is injection into tissue such as intratumoral injection.

As used herein, the terms "administering," "administration," and like terms refer to any method which, in sound medical practice, delivers a composition containing an active agent to a subject in such a manner as to provide a therapeutic or diagnostic effect. One aspect of the present subject matter provides for intravenous administration. Other suitable routes of administration can include parenteral, subcutaneous, oral, intramuscular, intratumoral or intraperitoneal. In some embodiments, the administration is intravenous injection and the composition comprises 1-200 carriers per a single cell of a tumor of the subject. In some embodiments, the administration is intratumoral injection and the composition comprises 1-20 carriers per a single cell of a tumor of the subject.

The dosage administered will be dependent upon the age, health, and weight of the recipient, kind of concurrent treatment, if any, frequency of treatment, and the nature of the effect desired.

The methods of the present invention may be used to preferentially target a vast number of target cell types. For example, contemplated target cells include, but are not limited to, hepatocytes, epithelial cells, hematopoietic cells, endothelial cells, lung cells, bone cells, stem cells, mesenchymal cells, neural cells, cardiac cells, adipocytes, vascular smooth muscle cells, cardio myocytes, skeletal muscle cells, beta cells, pituitary cells, synovial lining cells, ovarian cells, testicular cells, fibroblasts, B cells, T cells, reticulocytes, leukocytes, granulocytes and tumor cells. As used herein, "tumor cells" include primary cancer cells as well as metastatic cells.

As used herein, the term "subject" refers to any animal (e.g., a mammal), including, but not limited to, humans, non-human primates, rodents, and the like, to which the compositions and methods of the present invention are administered. In some embodiments, the terms "subject" and "patient" are used interchangeably herein in reference to a human subject. In other embodiments, the terms "subject" and "patient" are used interchangeably herein in reference to a non-human subject.

In some embodiments, the method of the invention is useful for determining or predicting the response of a subject afflicted with a malignant disease to a therapeutic agent. In some embodiments, said malignant disease is cancer, cancer metastasis and pre-malignant lesions. In some embodiments, the subject is afflicted with cancer. In some embodiments, the disease is an inflammatory disease. In some embodiments, the disease is a neurological disease. In some embodiments, the disease is a disease that would benefit from the death or decrease of a particular cell or cell type.

Examples of cancer therapeutic agents include, e.g., but are not limited to 4-hydroxycyclophosphamide, 5-FU, Abiraterone, Acitretin, Aldesleukin, Alemtuzumab, Amifostine, Amsacrine, Anagrelide, Anastrozole, Arsenic, Asparaginase, Asparaginase Erwinia, Axitinib, azaCITltidine, BCG, Bendamustine, Bevacizumab, Bexarotene, Bicalutamide, Bleomycin, Bortezomib, Brentuximab, Bromocriptine, Buserelin, Busulfan, Cabazitaxel, Cabergoline, Capecitabine, CARBOplatin, Carmustine, Cetuximab, Chlorambucil, CISplatin, Cladribine, Clodronate, Crizotinib, Cyclophosphamide, CycloSPORINE, Cytarabine, Dacarbazine, Dactinomycin, Dasatinib, DAUNOrubicin, Degarelix, Denosumab, Dexamethasone, Dexrazoxane, DOCEtaxel, DOXOrubicin, DOXOrubicin pegylated liposomal, Enzalutamide, Epirubicin, Eribulin, Erlotinib, Estramustine, Etoposide, Everolimus, Exemestane, Filgrastim, Fludarabine, Fluorouracil, Flutamide, Fulvestrant, Gefitinib, Gemcitabine, Goserelin, Hydroxyurea, IDArubicin, Ifosfamide, Imatinib, Iniparib, Interferon alfa-2b, Ipilimumab, Irinotecan, Ixabepilone, Lambrolizumab, Lanreotide, Lapatinib, Lenalidomide, Letrozole, Leucovorin, Leuprolide, Lomustine, Mechlorethamine, medroxyPROGESTERone, Megestrol, Melphalan, Mercaptopurine, Mesna, Methotrexate, mitoMYCIN, Mitotane, mitoXANTRONE, Nilotinib, Nilutamide, Octreotide, Ofatumumab, Oxaliplatin, PACLitaxel, PACLitaxel nanoparticle, albumin-bound (nab), Pamidronate, Panitumumab, Pazopanib Pemetrexed, Pertuzumab, Porfimer, Procarbazine, Quinagolide, Raltitrexed, Reovirus Serotype 3-Dearing Strain, riTUXimab, Romidepsin, Ruxolitinib, SORAfenib, Streptozocin, SUNItinib, Tamoxifen, Temozolomide, Temsirolimus, Teniposide, Testosterone, Thalidomide, Thioguanine, Thiotepa, Thyrotropin alfa, Tocilizumab, Topotecan, Trastuzumab (HERCEPTIN®), Trastuzumab, Emtansine (KADCYLA®), Treosulfan, Tretinoin, Vemurafenib, vinBLAstine, vincristine and Vinorelbine.

Examples of chemotherapeutic agents used as a therapeutic agent include, e.g., but are not limited to, e.g., alkylating agents (e.g., cyclophosphamide, ifosfamide, melphalan, chlorambucil, aziridines, epoxides, alkyl sulfonates), cisplatin and its analogues (e.g., carboplatin, oxaliplatin), antimetabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., vinca alkaloids, such as vincristine, vinblastine, and vinorelbine; taxanes, such as paclitaxel and docetaxel), interferons, interleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemestane, octreotide), octreotide, anti-androgens (e.g., flutamide, casodex), kinase and tyrosine inhibitors (e.g., imatinib (STI571 or Gleevac); gefitinib (Iressa); and erlotinib (Tarceva), etc. See, e.g. Cancer: Principles and Practice of Oncology, 7th Edition, Devita et al, Lippincott Williams & Wilkins, 2005, Chapters 15, 16, 17, and 63).

In some embodiments, the method of the invention is useful for determining or predicting the response of a subject afflicted with an inflammatory disease or disorder to a therapeutic agent.

In some embodiments, the method of the invention is useful for determining or predicting the response of a subject afflicted with a degenerative disease or disorder to a therapeutic agent.

In some embodiments, the method of the invention is useful for determining or predicting the response of a subject afflicted with a neurological disease or disorder to a therapeutic agent.

By another aspect there is provided a composition comprising bodily fluid substantially depleted of intact cells, wherein the bodily fluid substantially depleted of intact cells comprises at least one barcode uniquely identifying at least one therapeutic agent. In some embodiments, the bodily fluid is devoid of any intact cells. In some embodiments, the bodily fluid comprises a plurality of barcodes. In some embodiments, the bodily fluid is substantially depleted of intact carriers. In some embodiments, the bodily fluid is substantially depleted of intact liposomes. In some embodiments, the bodily fluid comprises cftDNA. In some embodiments, the barcodes are cftDNA. In some embodiments, the composition is for use in predicting the response of a subject afflicted with a disease to a therapeutic agent.

As used herein, the term "about" when combined with a value refers to plus and minus 10% of the reference value. For example, a length of about 1000 nanometers (nm) refers to a length of 1000 nm+-100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Example 1: Equal Numbers of Liposomes, with Equal Relative Drug Concentrations are Required for Accurate Evaluation of Efficacy An experiment was run to test the ideal dose of each drug to be included in the liposome mixture for theranostic use. Liposomes loaded with doxorubicin (barcode 2), gemcitabine (barcode 3) or cisplatin (barcode 4) were generating according to a preexisting protocol (see international patent publication WO2016024281, which is herein incorporated by reference in its entirety). For each batch of liposomes, the lipid concentration, encapsulated drug concentration, size distribution and zeta potential were measured. The results are summarized in Table 1. Because all the different batches are of liposomes with the same lipid composition (55 mole % HSPC, 40 mole % Cholesterol and 5 mole % DSPE-PEG) and size (~100 nm) it was assumed that the lipid concentration (evaluated by Stewart assay) and derived amount (in moles) of lipids are proportional to the total number of liposomes in each batch.

TABLE 1

Analysis of liposome batches

| Drug-barcode-liposome | Lipid concentration (mM) | Encapsulated Drug concentration (mg/ml) | Size distribution of liposomes (nm) | Zeta potential (mV) | Effective therapeutic dose (ETD) (mg/kg) |
|---|---|---|---|---|---|
| DOX-ds2-lipo | 30.73 | 2.16 | 99.8 | −20.13 | 5 |
| GEM-ds3-lipo | 49.05 | 0.96 | 98.6 | −19.1 | 125 |
| CIS-ds4-lipo | 51.43 | 0.13 | 99.3 | −19.5 | 6 |

Each drug has its own specific effective therapeutic dose (MTD), and in order to test efficacy it is reasonable that each liposome mix (a mix of all three types of liposomes to be injected together) should have the same relative amount of each drug. That is, in order to determine an ideal dose, batches of mixed liposomes were generated in which all three drugs were present in a concentration that was either 5%, 1% or 0.1% of the effective therapeutic dose. Table 2 provides the amounts (in ul) of each liposome batch that were added to the mix in order to provide each total dose.

TABLE 2

Liposome mix composition

| | GEM-ds3-lipo | CIS-ds4-lipo | DOX-ds2-lipo |
|---|---|---|---|
| 5% dose mix | 130 | 46 | 2.3 |
| 1% dose mix | 26 | 9.2 | 0.46 |
| 0.1% dose mix | 2.6 | 0.9 | 0.046 |

Figure 1B:
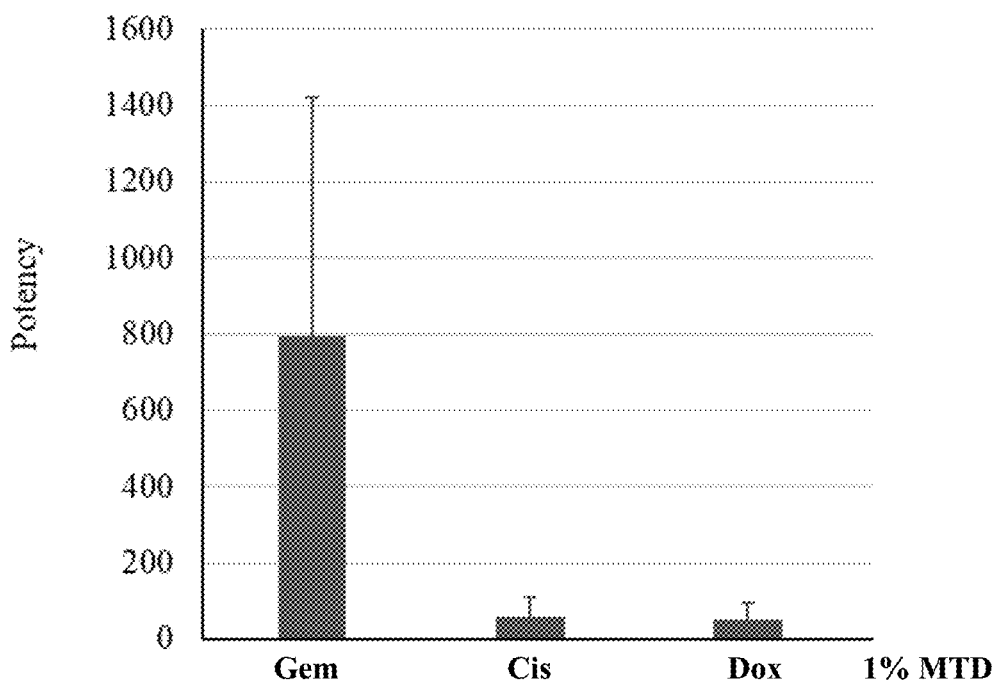
Figure 1C:
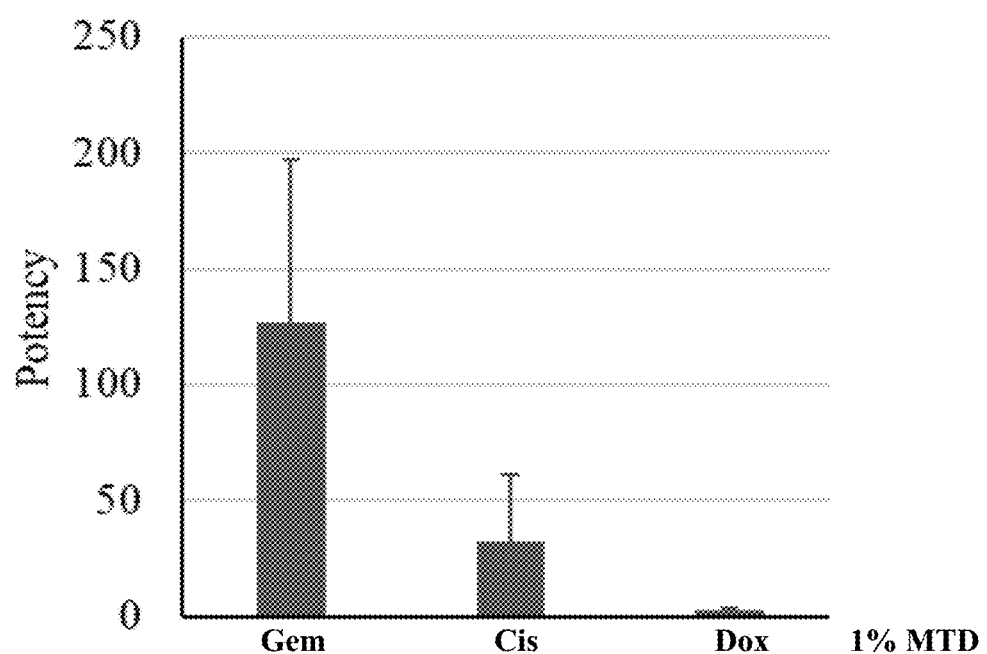

Cell from a triple negative breast cancer tumor were transplanted to the fat pad of BALB/c female mice and allowed to grow to form tumors in the mice. The mice were separated into 3 groups and then each group was injected with the 5%, 1% or 0.1% liposome mixes. 48 hours post injection the tumors were excised, and live/dead cell analysis was performed by FACS, followed by barcode analysis in live and dead cells separately. Gemcitabine was found to be the most effective treatment regardless of concentration used, but unexpectedly it was found to be upwards of 10-fold more effective than the other two drugs (FIG. 1A-C) Based on previous experiments with the same tumor cells, this extreme superiority of gemcitabine was not expected, and indeed was likely to be an artifact of the analysis is some way.

Gemcitabine has a greater than 20 times higher effective therapeutic dose than doxorubicin or cisplatin; however, it was not integrated into liposomes at significantly higher concentrations. Further, significantly more liposomes comprising gemcitabine and cisplatin were generated than comprising doxorubicin (see Table 1). Thus, in order than there should be even relative doses many more gemcitabine containing liposomes were injected than the other two drugs, and in fact many more cisplatin containing liposomes were injected than doxorubicin containing. By multiply the volume of each liposome batch added to the mix by the lipid concentration for each batch we arrive at the realization that the relative concentration of liposomes between gemcitabine, cisplatin and doxorubicin is 91:33:1. That is for every 1 liposome containing dox, there were 33 containing cisplatin and 91 containing gemcitabine. This would explain the bias in the results.

Since these drugs were effective (barcodes could be detected from dead cells) even at the very low dose of 0.1%, it was determined that equality in dosing is less significant that equality in liposome number. Certainly, the dose should not differ from one batch of liposomes to the next by a large amount, for instance not more than 1% of the MTD, but for all future experiments it was determined that the loading of each liposome type into the mix would be determined by the lipid concentration. Equality in drug concentration was still important, but equal liposome numbers was most important and subsequently drug concentration would be equalized to as great an extent as possible.

Example 2: Theranostic Detection in Liquid Biopsy

With method of generating a liposome mix that produced more accurate results in hand, it was hypothesized that the barcode analysis could be performed not only on tumor biopsies, but on cell free tumor DNA (cftDNA) circulating in the blood stream. The mouse 4T1 breast tumor model was used to test the feasibility of the liposome barcodes for theranostic use in blood. 4T1 mammary carcinoma cancer cells were grown in standard tissue culture conditions. 50 μl of $6 \times 10^6$ cells/ml of 4T1 cells ($3 \times 10^5$ cells/mouse) were injected subcutaneously to the left, front nipple of 8-week-old BALB/c female mice. From injection, weight and tumor size (length and width) as well as physical condition of animals were recorded every 2-3 days. The tumor volume was measured with a caliper and calculated as length/$2 \times$ (width)$^2$.

Three types of liposomes were tested together in a mix: doxorubicin containing (barcode 2), gemcitabine containing (barcode 3), and cisplatin containing (barcode 4) (see Table 3). 4T1 cells are highly sensitive to cisplatin, but less so to doxorubicin and even less so to gemcitabine. Further, these cells have been shown to become resistant to doxorubicin and though gemcitabine retards tumor growth within the first couple of days of treatment it has been found to not be effective at later time points (Kiew et al., 2012, Efficacy of a poly-L-glutamic acid-Gemcitabine conjugate in tumor-bearing mice, Drug Dev. Res. 73: 120-129).

Liposomes were composed of 55 mole % hydrogenated soybean phosphatidylcholine (HSPC), 5 mole % polyethylene glycol distearoyl-phosphoethanolamine (m2000PEG- DSPE), and 40 moles % cholesterol. Initial loading concentration of the lipid was 50 mM. To form liposomes, lipids were dissolved in absolute ethanol, warmed to 65° C. and injected to 1 ml of the appropriate barcoded solution. The liposomes were downsized by two consecutive stepwise extrusion, using 800, 400, 200, 100, 80 nm and then 80, 50, 50 nm pore-size polycarbonate membranes in a Lipex Extruder. After extrusion, the size was measured, using dynamic light scattering. The polydispersity index was between 0.05 and 0.09 and particle size 90±10 nm. As all liposomes had roughly the same particle size and the same lipid composition, lipid concentration was once again an effective way of measuring the total number of liposomes. Since some liposomes are lost during extrusion and loading of the various therapeutic agents, therefore the lipid concentration was measured after loading to ensure that final mixes were generated with equal numbers of each liposome (see Table 4).

TABLE 3

Liposome composition

| Liposomal Content | Batch name | Lot# | Lipid concentration (mM) | Liposomal Drug concentration (mg/ml) |
|---|---|---|---|---|
| Doxorubicin HCl | DOX-ds2-lipo | BDT-180525D2 | 31 | 0.069 |
| Gemcitabine HCl | GEM-ds3-lipo | BDT-180524G3 | 33 | 0.96 |
| Cisplatin | CIS-ds4-lipo | BDT-180524C4 | 37 | 0.13 |

Doxorubicin-HCl was actively loaded into liposomes via ammonium sulfate (120 mM) gradient, whereas Gemcitabine and Cisplatin were passively loaded in ammonium sulfate (120 mM) and 0.9% NaCl, respectively. Non-encapsulated barcodes and drugs were removed by dialysis, using a 1000 kDa and 12-14 kDa MW cutoff membrane, respectively. The final drug containing liposomes were filtered via 0.2 μm and stored at refrigerated condition (2° C.-8° C.) protected from light.

The various types of liposomes had close to equal amounts of total liposomes (31:33:37), further 14 times more gemcitabine than doxorubicin and more than 7 times more gemcitabine than cisplatin was loaded. A liposome mix (LPM) was generated with equal numbers of all three liposomes, as is described in Table 4. Because the doxorubicin containing batch had the lowest lipid concentration more of this type of liposome was added to the mix (20 ul vs 18.78 for gemcitabine and 16.67 for cisplatin). By multiplying the volume of liposomes added by the drug concentration the percent of the MTD could be calculated. Though 0.1% MTD was found to be effective, this LPM was designed to have roughly 1% of the MTD. Since the mix was designed with equal liposome number in mind, the dose was not perfectly even, however all the drugs were close to 1% of the MTD, and all were above the 0.1% threshold and thus should be effective. Sucrose-histidine buffer, pH=6.5, was used as the carrier for the liposomes, and a final volume of 150 ul was injected into each mouse's lateral tail vein when tumor volume reached~100-300 mm$^3$.

TABLE 4

LPM preparation

| Liposomal Drug and buffer | Lipids conc. (mM) | Drugs conc. (mg/ml) | Lipid conc. ratio to DOX-ds2 | in 150 ul injection (ul) | Therapeutic dose (mg/kg) | % of therapeutic dose in LPM |
|---|---|---|---|---|---|---|
| DOX-ds2 | 31 | 0.069 | 1.00 | 20.00 | 5 | 1.4% |
| GEM-ds3 | 33 | 0.93 | 1.06 | 18.78 | 125 | 0.7% |
| CIS-ds4 | 37 | 0.12 | 1.20 | 16.67 | 6 | 1.7% |

At time points 0, 3, 24, 48, 72, 96 and 240 hours post LPM injection, animals were sacrificed, and blood withdrawn from the vena cava. Tumors were dissected from selected groups and stored in MACS storage solution for analysis as described below. A total of 23 mice participated were sacrificed according to the following groups:

TABLE 5

Experimental groups

| Group No | Time of Sacrifice (No of animals) | Tumor volume (mm$^3$) | LPM# |
|---|---|---|---|
| 1 | t = 0 (n = 3) | 331 286 266 | No injection |
| 2 | t = 3 (n = 3) | 232 192 189 | All 4 liposomes |
| 3 | t = 24 (n = 3) | 174 159 152 | All 4 liposomes |
| 4 | t = 48 (n = 5) | 149 147 140 140 135 | All 4 liposomes |
| 5 | t = 72 (n = 3) | 120 119 108 | All 4 liposomes |
| 6 | t = 96 (n = 3) | 106 91 82 | All 4 liposomes |
| 7 | t = 240 (n = 3) | 80 70 56 | All 4 liposomes |

Following sacrifice, 0.5-0.7 ml of blood was collected from each animal and when removed, tumors were processed or stored in 3 ml of MACS Tissue Storage Solution at 4° C. protected from light until processing. Blood samples were centrifuged twice at 1000×g for 15 min to obtain platelet-poor plasma. Plasma samples were frozen for later processing. For DNA extraction, samples were thawed at room temperature, 100 μl were set aside and any remaining plasma was refrozen. Barcodes were isolated using Nucleospin Virus kit (Macherey Nagel) according to manufacturer's instructions (see below for further details). Eluted samples were immediately subjected to real-time PCR analysis or frozen.

After dissociating the tumor tissue into a single-cell suspension, the cells were counted and stained using either Carboxyfluorescein diacetate succinimidyl Ester (CF SE) solution or Propidium Iodide (PI). The CFSE working solution (2.5 μg/μl) was diluted 1:1000 (1 μl of diluted CFSE in 1 ml of single-cell suspension). Cells were incubated with CFSE 30 min at 37° C. followed by washing (×3) in RPMI before sorting. PI stock (SIGMA) solution (1 mg/ml) was diluted 1:200 (5 μl of stock PI in 1 ml of single-cell suspension) 10-15 min before sorting. The cells were sorted using a flow-activated cell sorter (FACSARIA III, BD Biosciences, San Jose, Calif., USA), analyzed by FACS-DIVA™ SOFTWARE (BD Biosciences) and separated according to viability. A pure live cell population was thus obtained. Unstained cells were used as negative control.

Nucleic acid extraction was performed from liposomes, blood and live cell samples prior to Real Time PCR Analysis. Extraction from liposomes was performed using the Nucleospin Virus Kit according to manufacturer's instruction (Macherey-Nagel). For the live tumor cells, 200 μl of PBS was added to cell pellet obtained after FACS sorting. Nucleic acids (barcodes and genomic DNA) were extracted with the Nucleospin Virus Kit as follows. After lysis of the sample and adjusting binding conditions and before loading on the column, a centrifugation step was added (1 minute at 13,000 g) to the standard protocol to remove all solid debris from the sample. This avoids column clogging issues. Samples were eluted with 40 μl of pre-warmed nuclease free water. Final sample volumes were recorded. Elution was performed by two consecutive elutions (30 μl then 10 μl) and final eluted volume was 32 μl.

To quantify the barcodes, real-time RT-PCR was used. The different barcodes were analyzed using an Applied Biosystems 7300 Real-Time PCR System. The assay was run with TaqMan Fast Advanced master mix (ThermoFisher Scientific), primers (IDT) and a specific probe labeled on the 5' end with fluorescent FAM dye and on its 3' end with a non-fluorescent quencher linked to a Minor Groove Binder (MGB) (ThermoFisher Scientific). For quantitation of barcode copy number, a standard curve for each barcode was generated starting with the barcode stock (100 μM). After preparation of all dilutions, real-time PCR was used to validate the standard curve. A reaction was run for all barcodes together with the following components and settings:

TABLE 6

Real-time PCR components

| Reaction mix component | Volume per well (PCR strip tube, 20 μl) | x17 reactions |
|---|---|---|
| 2x fast advanced master mix (ThermoFisher Scientific) | 10 | 170 |
| Forward Pirmer (5 μM) | 0.4 | 6.8 |
| Reverse Primer (5 μM) | 0.4 | 6.8 |
| Probe (5 μM) | 0.4 | 6.8 |
| UPW | 6.8 | 115.6 |
| Total | 18 | |
| Template volume to be added | 2 | |

TABLE 7

Real-time PCR settings

| Stage | Temperature | Time |
|---|---|---|
| Hold | 50° C. | 2 min |
| Hold | 95° C. | 20 sec |

TABLE 7-continued

Real-time PCR settings

| Stage | Temperature | Time |
|---|---|---|
| PCR (40 cycles) | 95° C. | 3 sec |
|  | 60° C. | 30 sec |

Figure 2A:
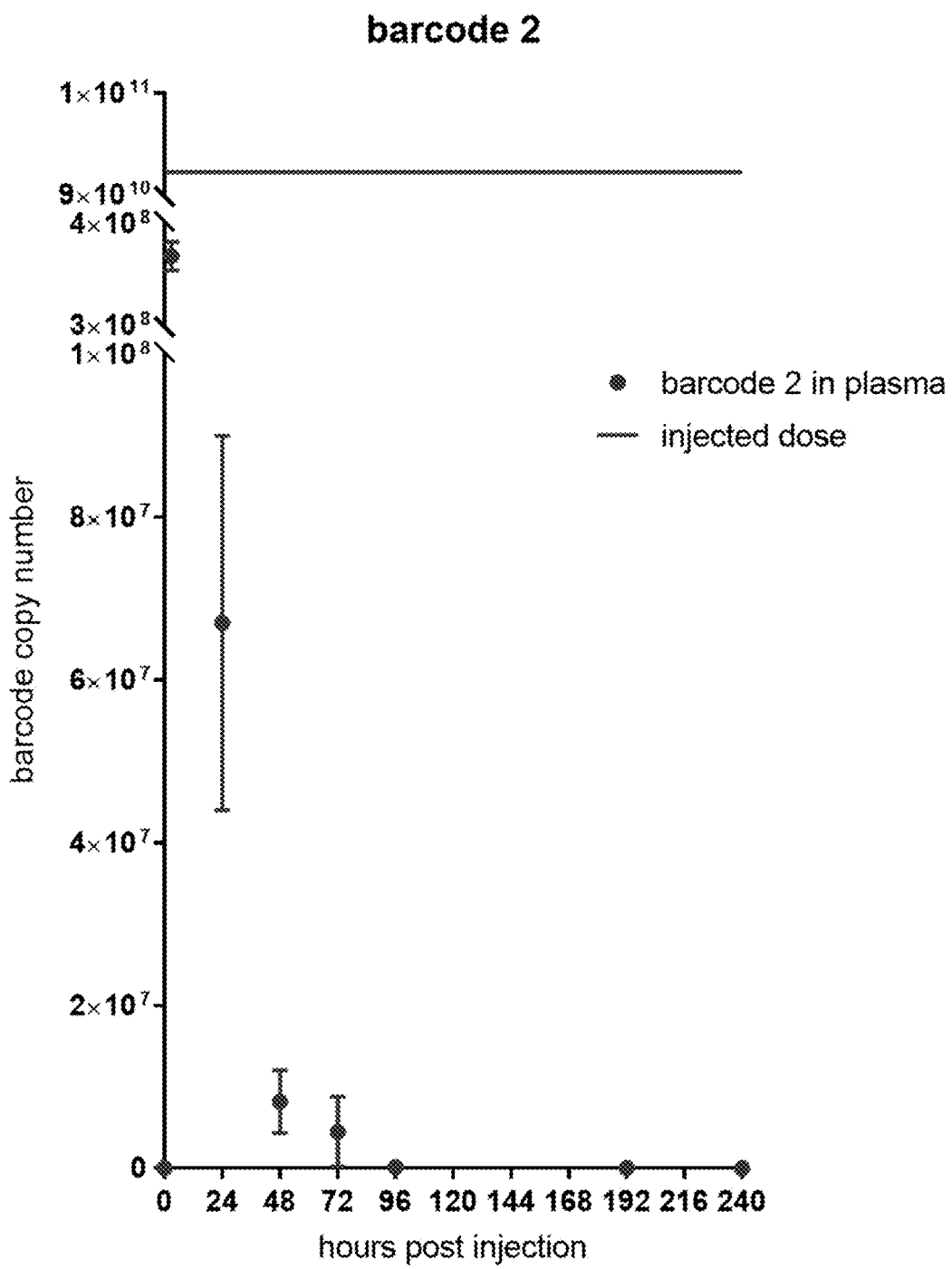
FIGS. 2A-D: Barcode detection level in plasma. Charts showing the copy number of barcodes 2, 3, 4 in plasma, which correspond to liposomes containing (2A) doxorubicin, (2B) gemcitabine, and (2C) cisplatin at different time points after injection. (2D) A combination of the charts of 2A-C with a common axis.
Figure 2B:
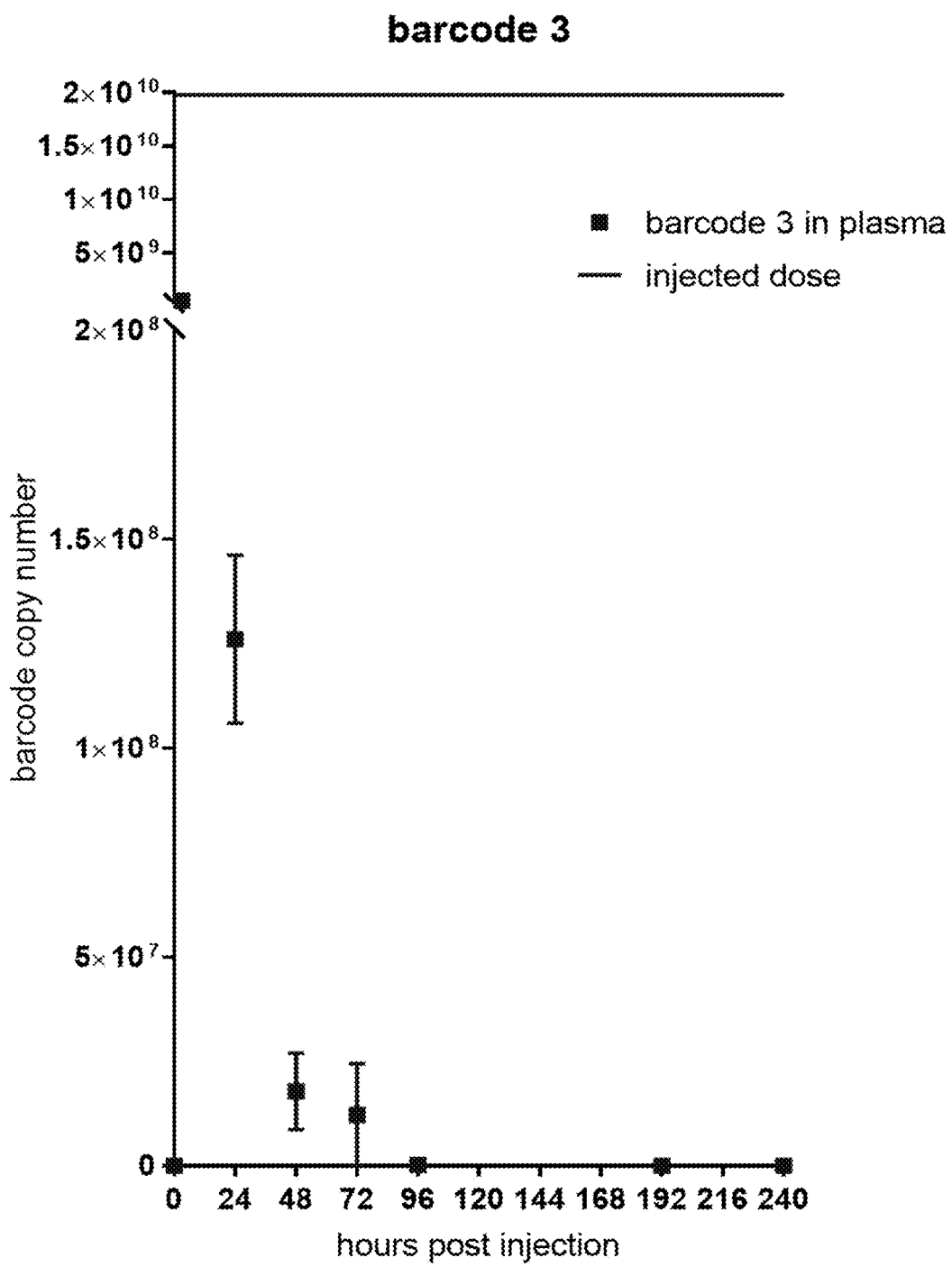
Figure 2C:
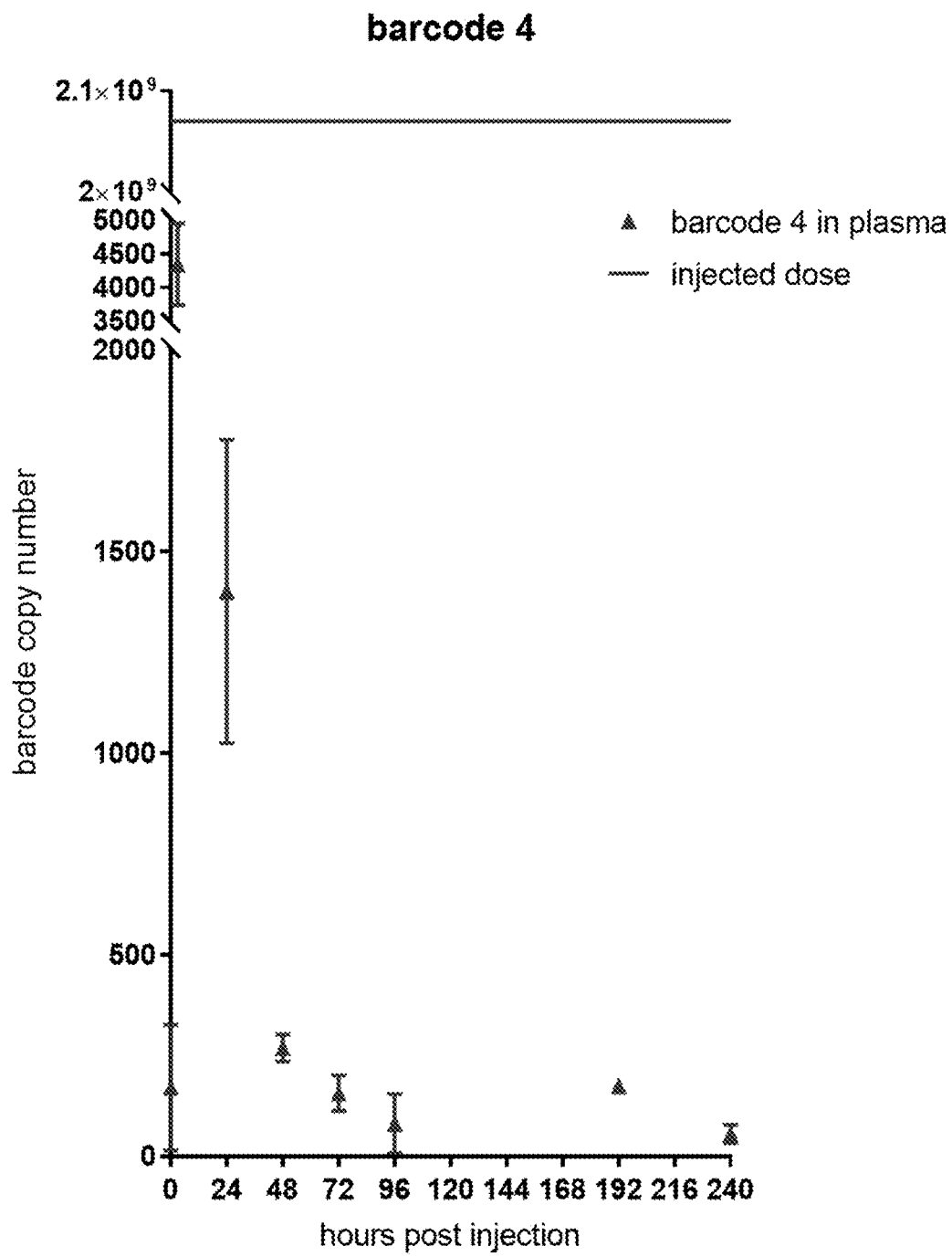
Figure 2D:
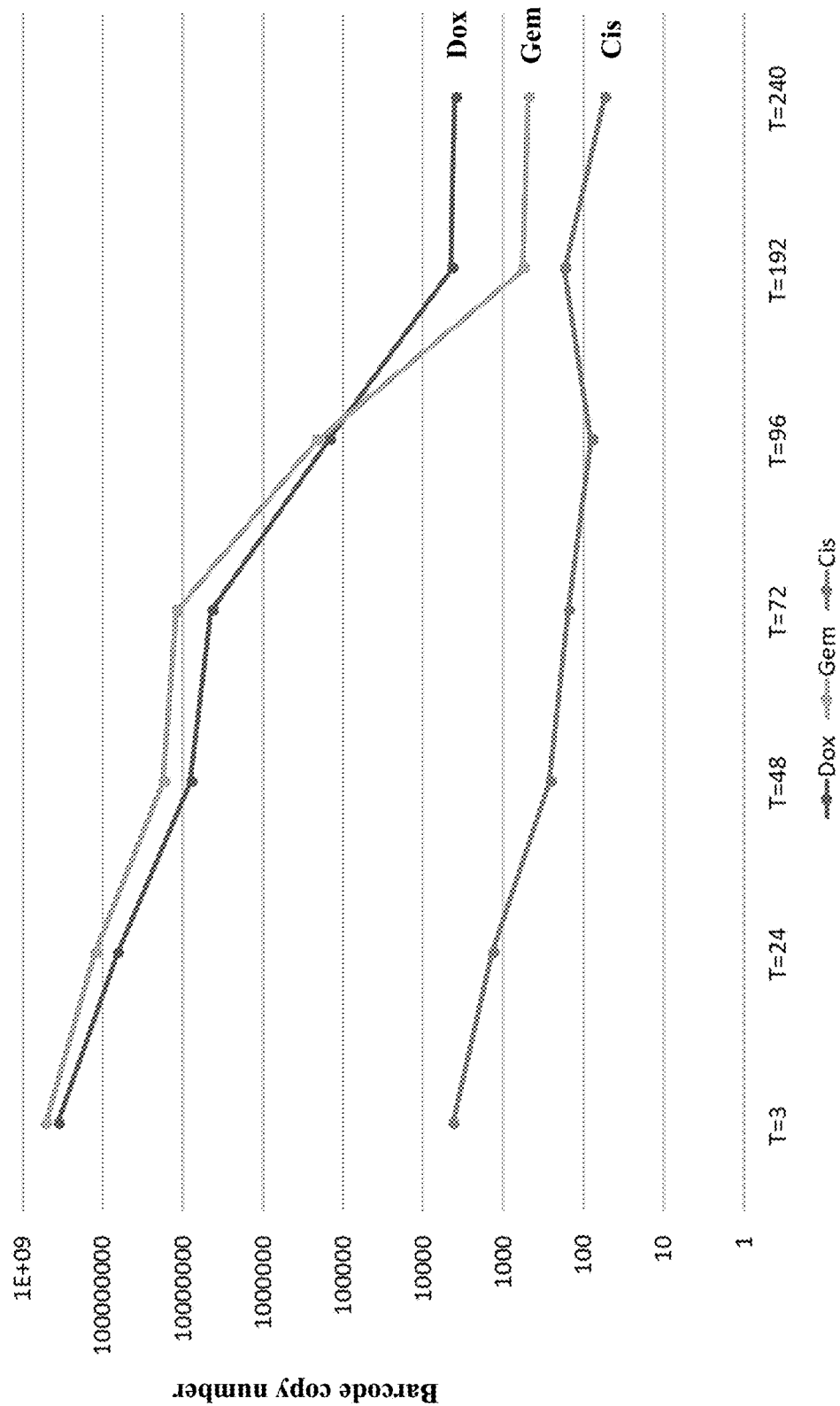

The PCR quantification was converted to barcode copy number (using the standard curve) and the results for the various barcodes are presented in FIGS. 2A-C. Immediately after injection the concentration of barcodes in the blood is very high and steadily drops over the following 4 days at which point a baseline level is reached. Results for all three barcodes plotted together are shown in FIG. 2D. Cisplatin binds to DNA and may partially inhibit detection by PCR. This would explain the significantly lower levels of the barcode 4 just 3 hours after injection. Nevertheless, the same trend of decreasing levels of circulating barcodes can be seen for all 3 liposome types. Significantly, barcode 4 showed a slight increase in barcode copy number at 192 hours, while the other two did not (FIG. 2D). An increase in barcode number is significant as no new source of barcodes was administered to the animal. Rather, this increase is likely due to apoptotic cells that were sensitive to cisplatin, that upon death released barcode 4 to the circulation as cftDNA which was subsequently detectable in the liquid biopsy. This proves that a liquid biopsy is an effective method for theranostic monitoring of drug efficacy in subjects.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for predicting response of a subject afflicted with cancer to at least one therapeutic agent of a plurality of therapeutic agents, the method comprising the steps of:
    (a) administering to the subject a composition comprising a plurality of types of carriers and said plurality of therapeutic agents, wherein each carrier is selected from a nanoparticle and a liposomal membrane and each type of carrier independently comprises between 0.1 and 10% of an effective therapeutic dose (ETD) of a different at least one therapeutic agent from among said plurality of therapeutic agents and one or more nucleic acid barcodes uniquely identifying said different at least one therapeutic agent from among said plurality of therapeutic agents;
    (b) obtaining a fluid sample from said subject, wherein said fluid is selected from the group consisting of: blood, plasma, serum, saliva, lymph, urine, breast milk, cerebral spinal fluid and seminal fluid; and
    (c) detecting, in said fluid, at least one of said unique nucleic acid barcodes of one type of carrier, wherein the presence of said unique nucleic acid barcode in said fluid indicates said subject's cancer responds to said different at least one therapeutic agent from among said plurality of therapeutic agents identified by said detected unique nucleic acid barcode;
  thereby predicting response of a subject afflicted with cancer to at least one therapeutic agent of a plurality of therapeutic agents.

2. The method of claim 1, wherein said composition comprises a substantially equal number of each type of carrier, wherein substantially equal is a variance of less than 10%.

3. The method of claim 1, wherein each type of carrier comprises a substantially equal barcode concentration wherein substantially equal is a variance of less than 10%.

4. The method of claim 1, wherein each type of carrier comprises a substantially equal concentration of said different at least one therapeutic agent from among said plurality of therapeutic agents relative to an effective therapeutic dose (ETD) of said different at least one therapeutic agent from among said plurality of therapeutic agents, wherein substantially equal is a variance of less than 10%.

5. The method of claim 1, wherein said administering is intravenous injection and said composition comprises 1-200 of each type of carrier per a single disease cell of said subject.

6. The method of claim 1, wherein said administering is intratumoral injection, and said composition comprises 1-20 of each type of carrier per a single disease cell of said subject.

7. The method of claim 1, wherein said obtaining is performed within a time frame of 48-192 hours following said administering of said composition.

8. The method of claim 1, wherein said detecting comprises sequencing said nucleic acid barcode, amplifying said nucleic acid barcode, or both.

9. The method of claim 1, wherein said fluid is blood.

10. The method of claim 1, further comprising removing intact cells from said fluid sample before step (c).

11. The method of claim 1, further comprising removing intact carrier from said fluid sample before step (c).

12. The method of claim 1, wherein said at least one carrier further comprises a tag.

13. The method of claim 1, wherein said unique barcode comprises a cleavage site specific to a nuclease specific to said cancer.

14. The method of claim 1, wherein said unique barcode comprises a cleavage site specific to a nuclease with cytoplasmic localization in a cell of said disease.

15. The method of claim 1, wherein each type of carrier comprises between 0.1% and 5% of the ETD of said different at least one therapeutic agent from among said plurality of therapeutic agents.

16. The method of claim 1, wherein said detecting is detecting cell free DNA barcodes.

* * * * *